(12) United States Patent
Albrecht et al.

(10) Patent No.: US 12,122,745 B2
(45) Date of Patent: Oct. 22, 2024

(54) PROCESSES FOR PREPARING ALDARIC, ALDONIC, AND URONIC ACIDS

(71) Applicant: Archer Daniels Midland Company, Decatur, IL (US)

(72) Inventors: Karl Albrecht, Decatur, IL (US); James Brazdil, Leland, NC (US); Andrew Ingram, Champaign, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 0 days.

(21) Appl. No.: 17/777,341

(22) PCT Filed: Nov. 16, 2020

(86) PCT No.: PCT/US2020/060711
§ 371 (c)(1),
(2) Date: May 17, 2022

(87) PCT Pub. No.: WO2021/101834
PCT Pub. Date: May 27, 2021

(65) Prior Publication Data
US 2023/0028813 A1    Jan. 26, 2023

Related U.S. Application Data

(60) Provisional application No. 62/936,873, filed on Nov. 18, 2019.

(30) Foreign Application Priority Data

Jan. 29, 2020 (EP) .................................. 20154273

(51) Int. Cl.
*C07C 51/235* (2006.01)
*C07C 51/64* (2006.01)

(52) U.S. Cl.
CPC ............ *C07C 51/235* (2013.01); *C07C 51/64* (2013.01)

(58) Field of Classification Search
CPC ..... C07C 51/64; C07C 51/235; C07C 59/105; C07C 59/285
See application file for complete search history.

(56) References Cited

U.S. PATENT DOCUMENTS 7,982,031 B2 * 7/2011 Kowalczyk .............. B01J 23/52
                                                            536/124
9,776,945 B2 * 10/2017 Diamond ................ C07C 51/27

OTHER PUBLICATIONS

Jin, X., et al., Syngistic effects of bimetallic PtPd/TiO2 nanocatalysts in oxidation of glucose to glucaric acid: Structure depenent activity and selectivity, I&EC Research, vol. 55, No. 11, pp. 2932-2945 (Year: 2016).*

Venema, F.R., et al., Platinum catalyzed oxidation of aldopentose to aldaric acids, Journal of Molecular Catalysis, vol. 77, pp. 75-85 (Year: 1992).*

* cited by examiner

*Primary Examiner* — Yate' K Cutliff
(74) *Attorney, Agent, or Firm* — William B. Miller

(57) ABSTRACT

Various processes for preparing aldaric acids, aldonic acids, uronic acids, and/or lactone(s) thereof are described. For example, processes for preparing a $C_5$-$C_6$ aldaric acid and/or lactone(s) thereof by the catalytic oxidation of a $C_5$-$C_6$ aldonic acid and/or lactone(s) thereof and/or a $C_5$-$C_6$ aldose are described.

14 Claims, 13 Drawing Sheets

PROCESSES FOR PREPARING ALDARIC, ALDONIC, AND URONIC ACIDS

CROSS-REFERENCE TO RELATED APPLICATIONS

This application is a national stage entry of International Application No. PCT/US20/60711, filed Nov. 16, 2020, which itself claims priority to U.S. Provisional Patent Application No. 62/936,873, filed Nov. 18, 2019, and EP Patent Application No. 20154273.5, filed Jan. 29, 2020, the contents of each are incorporated herein by reference.

FIELD OF THE INVENTION

Various processes for preparing aldaric acids, aldonic acids, uronic acids, and/or lactone(s) thereof are described. For example, processes for preparing a $C_5$-$C_6$ aldaric acid and/or lactone(s) thereof by the catalytic oxidation of a $C_5$-$C_6$ aldonic acid and/or lactone(s) thereof and/or a $C_5$-$C_6$ aldose are described.

BACKGROUND OF THE INVENTION

For many years, there has been an interest in using biorenewable materials as a feedstock to produce commercially useful chemicals. In particular, a significant body of work has focused on the oxidation of sugars obtained from these materials to aldaric acids, especially glucose to glucaric acid. For example, see U.S. Pat. Nos. 8,669,397 and 8,785,683, which are incorporated herein by reference. Not only are these products useful as intermediates in the production of monomers such as adipic acid, but also in the production of compositions having commercial applications such as de-icing fluids, acidulants, detergent builders, pH regulators, chelants, de-scalers, corrosion inhibitors, metal cleaning and finishing agents, and components of cement formulations.

Numerous catalysts and reaction conditions have been attempted for these oxidation processes. However, sustained high yields of glucaric acid over prolonged operation or at high reactor throughputs have not been demonstrated. For example, in Lee et al., "Pt catalysts for efficient aerobic oxidation of glucose to glucaric acid in water," *Green Chemistry* 2016, 18 (13), 3815-3822 a glucaric acid yield of 74% is reported for the oxidation of a 5 wt. % glucose feed over a 5 wt. % Pt/C catalyst at 80° C. and about 200 psi O2 partial pressure in a batch reactor after 10 h of reaction. In U.S. Pat. No. 9,770,705, a glucaric acid yield of 70% is reported for an experiment where 2.3 mL of 10 wt. % gluconic acid feed was contacted with 75 mg of catalyst at 112-126° C. for 2-5 h. There remains a need for efficient and cost-effective processes for preparing aldaric acids, such as glucaric acid, and intermediates thereof from biorenewable materials that exhibit improved and stable yields, especially over prolonged operation and high reactor throughput.

Further, in the catalytic oxidation of aldoses to aldaric acids such as glucose to glucaric acid, catalyst inhibition has been observed during the reaction. See, for example, Jin et. al., "Synergistic Effects of Bimetallic PtPd/$TiO_2$ Nanocatalysts in Oxidation of Glucose to Glucaric Acid: Structure Dependent Activity and Selectivity," *Ind. Eng. Chem. Res.* 2016, 55, 2932-2945. However, the causes of inhibition are not fully understood and effective solutions for reducing or eliminating inhibition have not been developed. Thus, there remains a need for identifying the source(s) of inhibition of the oxidation reaction and solutions to address this problem while increasing product yield.

BRIEF SUMMARY OF THE INVENTION

Various aspects of the present invention are directed to processes for preparing a $C_5$-$C_6$ aldaric acid (e.g., glucaric acid) and/or lactone(s) thereof. In some embodiments, processes for preparing a $C_5$-$C_6$ aldaric acid and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ aldaric acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

In certain embodiments, processes for preparing a $C_5$-$C_6$ aldaric acid and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a separation zone to separate at least a portion of the oxidation reaction inhibitor from the feed mixture and form a first fraction comprising the oxidation reactant and a second fraction comprising the oxidation reaction inhibitor. At least a portion of the first fraction comprising the oxidation reactant is fed to a reaction zone and the oxidation reactant is reacted in the presence of oxygen and an oxidation catalyst in the reaction zone to form a reaction mixture comprising the $C_5$-$C_6$ aldaric acid and/or lactone(s) thereof.

In further embodiments, processes for preparing a $C_5$-$C_6$ aldaric acid and/or lactone(s) thereof comprise feeding a feed mixture comprising at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof to a reaction zone and reacting the oxidation reactant in the presence of oxygen and an oxidation catalyst in the reaction zone to form a reaction mixture comprising (a) the $C_5$-$C_6$ aldaric acid and/or lactone(s) thereof, (b) unreacted oxidation reactant(s) and/or on-path intermediate(s) thereof, and (c) an oxidation reaction inhibitor. The reaction mixture is fed to a separation zone to separate at least a portion of the $C_5$-$C_6$ aldaric acid and/or lactone(s) thereof from the reaction mixture and form a product fraction comprising the $C_5$-$C_6$ aldaric acid and/or lactone(s) thereof and a recycle fraction comprising the unreacted oxidation reactant(s) and/or on-path intermediate(s) thereof and the oxidation reaction inhibitor. A first portion of the recycle fraction is removed from the process (e.g., discharged as waste, directed elsewhere for further processing, etc.) and a second portion of the recycle fraction is recycled to the reaction zone or feed thereto.

Additional aspects of the present invention are directed to processes for preparing a $C_5$-$C_6$ uronic acid (e.g., guluronic acid) and/or lactone(s) thereof. In various embodiments, processes for preparing a $C_5$-$C_6$ uronic acid and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ uronic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

In certain embodiments, processes for preparing a $C_5$-$C_6$ uronic acid and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a separation zone to separate at least a portion of the oxidation reaction inhibitor from the mixture and form a first fraction comprising the oxidation reactant and a second fraction comprising the oxidation reaction inhibitor. At least a portion of the first fraction comprising the oxidation reactant is fed to a reaction zone and the oxidation reactant is reacted in the presence of oxygen and an oxidation catalyst in the reaction zone to form a reaction mixture comprising the $C_5$-$C_6$ uronic acid and/or lactone(s) thereof.

In other embodiments, processes for preparing a $C_5$-$C_6$ uronic acid and/or lactone(s) thereof comprise feeding a feed mixture comprising at least one oxidation reactant selected from the group consisting of a $C_5$-$C_6$ aldose, a $C_5$-$C_6$ aldonic acid and/or lactone(s) thereof, and mixtures thereof to a reaction zone and reacting the oxidation reactant in the presence of oxygen and an oxidation catalyst in the reaction zone to form a reaction mixture comprising (a) the $C_5$-$C_6$ uronic acid and/or lactone(s) thereof, (b) unreacted oxidation reactant(s) and/or on-path intermediate(s) thereof, and (c) an oxidation reaction inhibitor. The reaction mixture is fed to a separation zone to separate at least a portion of the $C_5$-$C_6$ uronic acid and/or lactone(s) thereof from the reaction mixture and form a product fraction comprising the $C_5$-$C_6$ uronic acid and/or lactone(s) thereof and a recycle fraction comprising the unreacted oxidation reactant(s) and/or on-path intermediate(s) thereof and the oxidation reaction inhibitor. A first portion of the recycle fraction is removed from the process (e.g., discharged as waste, directed elsewhere for further processing, etc.) and a second portion of the recycle fraction is recycled to the reaction zone or feed thereto.

Other aspects of the present invention are directed to processes for preparing a $C_5$-$C_6$ aldonic acid (e.g., gluconic acid) and/or lactone(s) thereof. In various embodiments, processes for preparing a $C_5$-$C_6$ aldonic acid and/or lactone(s) thereof comprise feeding a feed mixture comprising (a) an oxidation reactant comprising a $C_5$-$C_6$ aldose and (b) an oxidation reaction inhibitor to a reaction zone; and reacting the oxidation reactant in the presence of oxygen and an oxidation catalyst in the reaction zone to form a reaction mixture comprising the $C_5$-$C_6$ aldonic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

In certain embodiments, processes for preparing a $C_5$-$C_6$ aldonic acid and/or lactone(s) thereof comprise feeding a feed mixture comprising (a) an oxidation reactant comprising a $C_5$-$C_6$ aldose and (b) an oxidation reaction inhibitor to a separation zone to separate at least a portion of the oxidation reaction inhibitor from the mixture and form a first fraction comprising the oxidation reactant and a second fraction comprising the oxidation reaction inhibitor. At least a portion of the first fraction comprising the oxidation reactant is fed to a reaction zone and the oxidation reactant is reacted in the presence of oxygen and an oxidation catalyst in the reaction zone to form a reaction mixture comprising the $C_5$-$C_6$ aldonic acid and/or lactone(s) thereof.

In other embodiments, processes for preparing a $C_5$-$C_6$ aldonic acid and/or lactone(s) thereof comprise feeding a feed mixture comprising an oxidation reactant comprising a $C_5$-$C_6$ aldose to a reaction zone and reacting the oxidation reactant in the presence of oxygen and an oxidation catalyst in the reaction zone to form a reaction mixture comprising (a) the $C_5$-$C_6$ aldonic acid and/or lactone(s) thereof, (b) unreacted oxidation reactant(s) and/or on-path intermediate(s) thereof, and (c) an oxidation reaction inhibitor. The reaction mixture is fed to a separation zone to separate at least a portion of the $C_5$-$C_6$ aldonic acid and/or lactone(s) thereof from the reaction mixture and form a product fraction comprising the $C_5$-$C_6$ aldonic acid and/or lactone(s) thereof and a recycle fraction comprising the unreacted oxidation reactant(s) and/or on-path intermediate(s) thereof and the oxidation reaction inhibitor. A first portion of the recycle fraction is removed from the process (e.g., discharged as waste, directed elsewhere for further processing, etc.) and a second portion of the recycle fraction is recycled to the reaction zone or feed thereto.

Various aspects of the present invention are directed to processes for analyzing and/or upgrading a feed mixture. In some embodiments, a process for analyzing a feed mixture comprising at least one feed component selected from the group consisting of a $C_5$-$C_6$ aldose, a $C_5$-$C_6$ aldonic acid and/or lactone(s) thereof, a $C_5$-$C_6$ uronic acid and/or lactone(s) thereof, a $C_5$-$C_6$ aldaric acid and/or lactone(s) thereof, and mixtures thereof comprises analyzing the feed mixture to determine the components of the feed mixture and to determine the presence of any oxidation reaction inhibitor(s). In various embodiments, a process for preparing an upgraded feed mixture comprises analyzing the feed mixture as described herein to determine the presence of an oxidation reaction inhibitor; and separating at least a portion of the oxidation reaction inhibitor from the feed mixture in a separation zone to form a first fraction comprising the upgraded feed mixture and a second fraction comprising at least a portion of the oxidation reaction inhibitor.

Other objects and features will be in part apparent and in part pointed out hereinafter.

DETAILED DESCRIPTION OF THE INVENTION

Figure 1:
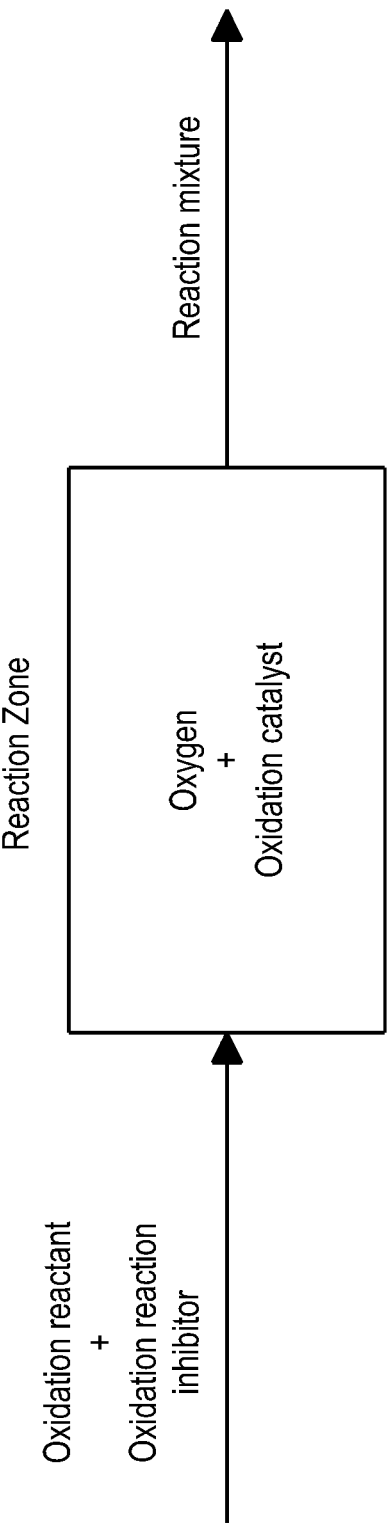
FIG. 1 presents a diagram depicting a process in accordance with various embodiments of the invention.

In accordance with the present invention, various processes described herein provide for enhanced conversion of oxidation reactant(s), improved yields of oxidation product(s), and/or greater process efficiency by reducing, limiting, or eliminating the amount of one or more compounds discovered to function as oxidation reaction inhibitors in the reaction zone. For example, various processes provide improved oxidation reaction feed mixtures having an oxidation reaction inhibitor concentration below a certain threshold (e.g., about 0.5 wt. % or less, about 0.3 wt. % or less, about 0.1 wt. % or less, about 0.05 wt. % or less, or about 0.01 wt. % or less). Further, various processes described herein provide for stable product yields over extended operation and/or at high reactor throughputs. These processes can advantageously improve process economics by decreasing the amount of off-path products that may require separation from the product mixture and/or decreasing the amount of on-path intermediates that require further processing.

Aldoses, as referred to herein, include various compounds possessing an aldehyde and hydroxyl groups, which can be represented by formula (I):

(I).

In various embodiments, the aldose comprises at least one C$_5$-C$_6$ aldose (i.e., where w in formula (I) is 3 or 4). In some embodiments, the aldose comprises at least one pentose and/or hexose. Specific C$_5$-C$_6$ aldoses include, for example, arabinose, lyxose, ribose, xylose, allose, altrose, galactose, glucose, gulose, idose, mannose, talose, and mixtures thereof. In various embodiments, the C$_5$-C$_6$ aldose comprises a hexose such as glucose. In some embodiments, the C$_5$-C$_6$ aldose comprises a pentose such as xylose, ribose, and/or arabinose. The term "aldoses" and any specific aldose mentioned herein and as defined by formula (I) also include cyclic forms (hemiacetal forms) of these compounds.

Aldoses can be obtained from various carbohydrate-containing sources including conventional biorenewable sources such as corn grain (maize), wheat, potato, cassava and rice, as well as alternative sources such as energy crops, plant biomass, agricultural wastes, forestry residues, sugar processing residues, and plant-derived household wastes. In various embodiments, the aldose (e.g., glucose) is obtained from a grain crop (e.g., corn, wheat, soybean, rice, barley, rye, millet, sorghum, etc.). More generally, biorenewable sources that can be used include any renewable organic matter that includes a source of carbohydrates such as, for example, switch grass, *miscanthus*, trees (hardwood and softwood), vegetation, and crop residues (e.g., bagasse and corn stover). Other sources include, for example, waste materials (e.g., spent paper, green waste, municipal waste, etc.). Carbohydrates can be isolated from biorenewable materials using known methods.

Aldonic acids, as referred to herein, include monocarboxylic acids of formula (II):

(II).

In various embodiments, the aldonic acid comprises at least one C$_5$-C$_6$ aldonic acid (i.e., where x in formula (II) is 3 or 4). In some embodiments, the aldonic acid comprises at least one pentonic acid and/or hexonic acid. Specific C$_5$-C$_6$ aldonic acids include, for example, arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof. In various embodiments, the C$_5$-C$_6$ aldonic acid comprises a hexonic acid such as gluconic acid. In some embodiments, the C$_5$-C$_6$ aldonic acid comprises a pentonic acid. For example, the pentonic acid can be selected from the group consisting of xylonic acid, ribonic acid, arabinonic acid, and mixtures thereof. Lactones of various aldonic acids can also be present and can be formed by intramolecular cyclocondensation of the acids.

Uronic acids, as referred to herein, include monocarboxylic acids of formula (III):

(III).

In various embodiments, the uronic acid comprises at least one C$_5$-C$_6$ uronic acid (i.e., where y in formula (III) is 3 or 4). In some embodiments, the uronic acid comprises at least one penturonic acid and/or hexuronic acid. Specific C$_5$-C$_6$ uronic acids include, for example, arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof. In various embodiments, the uronic acid comprises a hexuronic acid such as guluronic acid. In some embodiments, the uronic acid comprises a penturonic acid such as xylouronic acid, ribouronic acid, and/or arabinuronic acid. Lactones of various uronic acids can also be present and can be formed by intramolecular cyclocondensation of the acids. Also, the term "uronic acid" and any specific uronic acids mentioned herein and as defined by formula (III) also include cyclic forms (hemiacetal forms) of these compounds.

Aldaric acids, as referred to herein, include dicarboxylic acids of formula (IV):

(IV)

In various embodiments, the aldaric acid comprises at least one C$_5$-C$_6$ aldaric acid (i.e., where z in formula (IV) is 3 or 4). In some embodiments, the aldaric acid comprises at least one pentaric acid and/or hexaric acid. Specific C$_5$-C$_6$ aldaric acids include, for example, arabinaric acid, lyxaric acid, ribaric acid, xylaric acid, allaric acid, altraric acid, galactaric acid, glucaric acid, gularic acid, idaric acid, mannaric acid, talaric acid, and mixtures thereof. In various embodiments, the $C_5$-$C_6$ aldaric acid comprises a hexaric acid such as glucaric acid. In further embodiments, the $C_5$-$C_6$ aldaric acid comprises a pentaric acid selected from the group consisting of xylaric acid, ribaric acid, arabinaric acid, and mixtures thereof. Lactones of various aldaric acids can also be present and can be formed by intramolecular cyclocondensation of the acids. For example, lactones include glucarolactones such as D-glucaro-1,4-lactone, D-glucaro-6,3-lactone, and D-glucaro-1,4:6,3-dilactone.

The preparation of an aldaric acid and/or lactone(s) from an aldonic acid and/or lactone(s) and/or corresponding aldoses is typically a multistep synthesis that proceeds through various intermediates. For example, as shown in the scheme below, the oxidation of glucose to glucaric acid proceeds primarily through two intermediates: gluconic acid and guluronic acid.

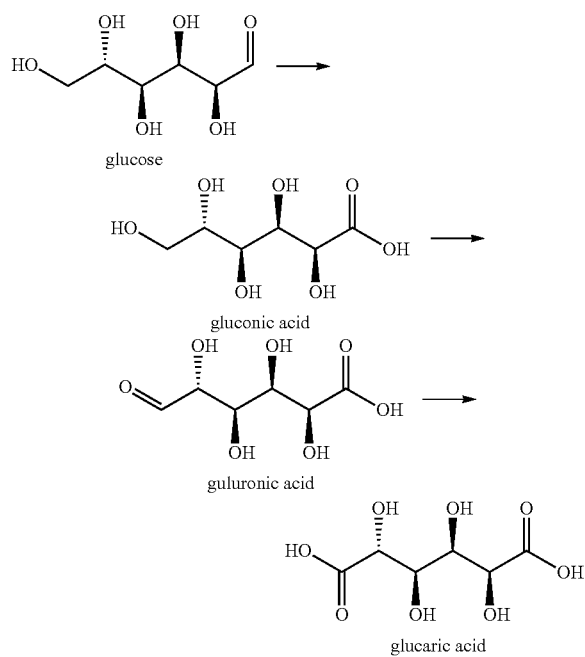

First, the carbonyl of glucose is oxidized to an acid, producing gluconic acid. Next, the terminal hydroxyl at the 6 position of gluconic acid is dehydrogenated to a carbonyl, resulting in guluronic acid. Finally, the carbonyl of guluronic acid is oxidized to an acid, forming glucaric acid.

Previously reported glucaric acid yields (e.g., yields rarely exceeding 70%) may be limited due to a number of factors. Some potential limiting factors include the formation of one or more oxidation reaction inhibitors which significantly reduce catalyst efficacy, over-conversion of glucaric acid, and leaching of catalytically active metals Also, without pH mediation via the continuous introduction of base during the oxidation reaction, the rate of glucaric acid production decreases as the pH decreases. On the other hand, pH mediation results in many cases of lower glucaric acid yields due to the over conversion of glucaric acid to sugar acid derivatives with less than 6 carbons. Thus, several inhibiting factors may contribute individually or in combination to limit the total yield to glucaric acid.

It has now been discovered that the presence of certain oxidation reaction inhibitors may negatively affect the conversion of a $C_5$-$C_6$ aldose, $C_5$-$C_6$ aldonic acid and/or lactone(s) thereof, $C_5$-$C_6$ uronic acid and/or lactone(s) thereof, and mixtures thereof and/or negatively affect yield of aldaric, aldonic, and uronic acids and/or lactone(s) thereof. For example, the reaction of a $C_5$-$C_6$ aldose, a $C_5$-$C_6$ aldonic acid and/or lactone(s) thereof, a $C_5$-$C_6$ uronic acid and/or lactone(s) thereof, and mixtures thereof wherein the reaction mixture comprises an oxidation reaction inhibitor may exhibit an overall conversion of 90% or less, 80% or less, 70% or less, 60% or less, 50% or less, 40% or less, 30% or less, or 20% or less as compared to a similar reaction having, for example, no more than 0.5 wt. % of an oxidation reaction inhibitor. Similarly, product yields in reactions where the concentration of the oxidation reaction inhibitor is not controlled can be 90% or less, 80% or less, 70% or less, 60% or less, 50% or less, 40% or less, 30% or less, or 20% or less of the yield observed in a similar reaction having, for example, no more than 0.5 wt. % of an oxidation reaction inhibitor.

Importantly, it has been found that certain $C_3$ compounds, particularly $C_3$ alcohols and/or $C_3$ acid can function as oxidation reaction inhibitors in the catalytic oxidation of $C_5$-$C_6$ aldose, $C_5$-$C_6$ aldonic acid and/or lactone(s) thereof, $C_5$-$C_6$ uronic acid and/or lactone(s) thereof, and mixtures thereof. Specific compounds that have been identified as oxidation reaction inhibitors include glyceric acid, 3-hydroxypropionic acid, 1,3-propanediol, and mixtures thereof. Accordingly, in various embodiments, the oxidation reaction inhibitor comprises at least one component selected from the group consisting of glyceric acid, 3-hydroxypropionic acid, 1,3-propanediol, and mixtures thereof. In some embodiments, the oxidation reaction inhibitor comprises glyceric acid. In certain embodiments, the oxidation reaction inhibitor comprises 3-hydroxypropionic acid.

It has also been found that the concentration of one or more of the oxidation reaction inhibitor(s) is related to the degree of inhibition observed. The processes described herein can advantageously provide for reduced concentrations of the oxidation reaction inhibitor in the reaction zone.

Processes for Producing Aldaric Acids and/or Lactone(s) Thereof

As noted, embodiments of the present invention include oxidation processes for producing aldaric acids (e.g., glucaric acid) and/or lactone(s) thereof. For example, various processes comprise feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ aldaric acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less. FIG. 1 presents a diagram depicting a process in accordance with these embodiments.

In various embodiments of these processes, the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Also, in some embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

Figure 2:
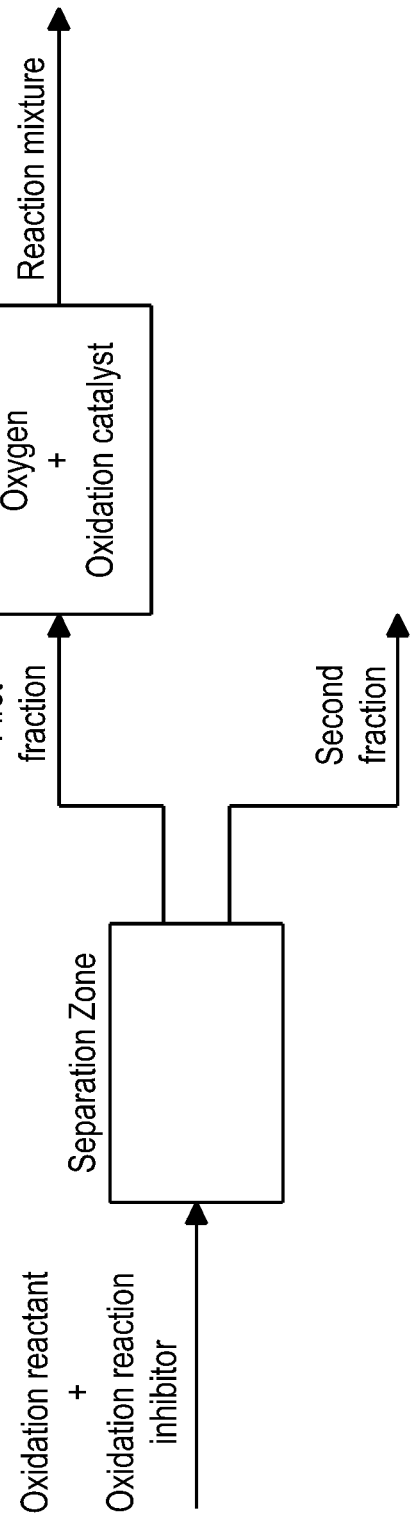
FIG. 2 presents a diagram depicting a process including a separation zone in accordance with various embodiments of the invention.

Other processes for preparing a $C_5$-$C_6$ aldaric acid (e.g., glucaric acid) and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a separation zone to separate at least a portion of the oxidation reaction inhibitor from the feed mixture and form a first fraction comprising the oxidation reactant and a second fraction comprising the oxidation reaction inhibitor; feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ aldaric acid and/or lactone(s) thereof. FIG. 2 presents a diagram depicting a process in accordance with these embodiments.

In various embodiments of these processes, the molar ratio of the oxidation reaction inhibitor to the oxidation reactant in the first fraction can be less than the molar ratio of the oxidation reaction inhibitor to oxidation reactant in the feed mixture. In some embodiments, the molar ratio of the oxidation reaction inhibitor to oxidation reactant in the first fraction is less than the molar ratio of the oxidation reaction inhibitor to oxidation reactant in the second fraction.

In various embodiments, the concentration of the oxidation reactant in the first fraction is about 1 wt. % or greater, about 5 wt. % or greater, about 10 wt. % or greater, about 15 wt. % or greater, or about 20 wt. % or greater. For example, the concentration of the oxidation reactant in the first fraction can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In some embodiments, the concentration of the oxidation reaction inhibitor in the first fraction can be less than the concentration of the oxidation reaction inhibitor in the second fraction. In various embodiments, the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less. For example, the concentration of the oxidation reaction inhibitor in the first fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Figure 3:
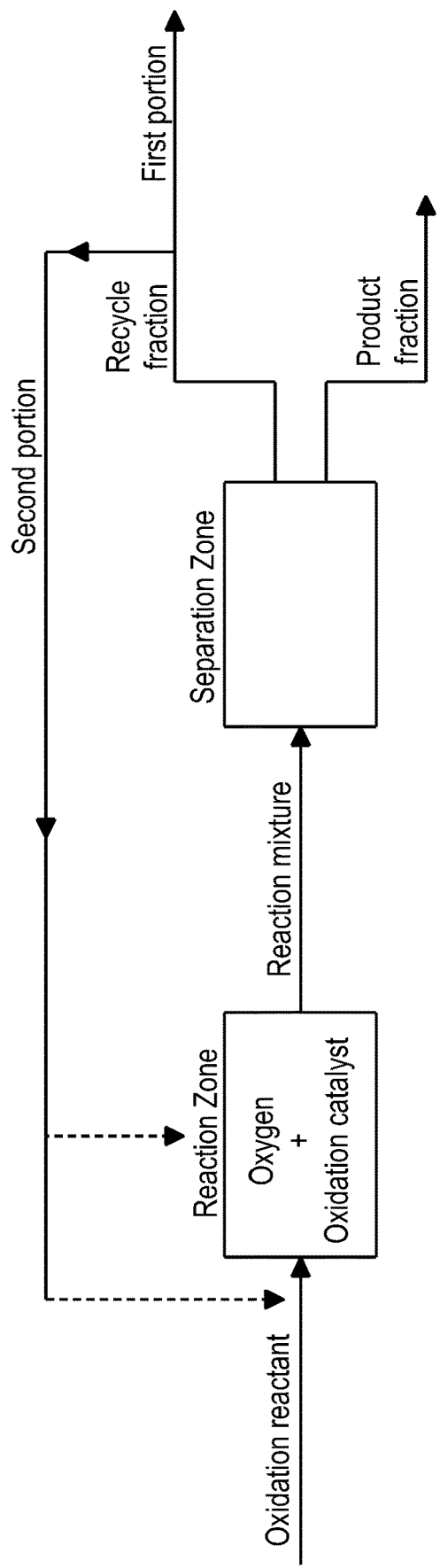
FIG. 3 presents a diagram depicting a process including a separation zone and recycle in accordance with various embodiments of the invention.

Further processes for preparing a $C_5$-$C_6$ aldaric acid (e.g., glucaric acid) and/or lactone(s) thereof comprise feeding a feed mixture comprising at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof to a reaction zone; reacting the oxidation reactant in the presence of oxygen and an oxidation catalyst in the reaction zone to form a reaction mixture comprising (a) the $C_5$-$C_6$ aldaric acid and/or lactone(s) thereof, (b) unreacted oxidation reactant(s) and/or on-path intermediate(s) thereof, and (c) an oxidation reaction inhibitor; feeding the reaction mixture to a separation zone to separate at least a portion of the $C_5$-$C_6$ aldaric acid and/or lactone(s) thereof from the reaction mixture and form a product fraction comprising the $C_5$-$C_6$ aldaric acid and/or lactone(s) thereof and a recycle fraction comprising the unreacted oxidation reactant(s) and/or on-path intermediate(s) thereof and the oxidation reaction inhibitor; removing a first portion of the recycle fraction from the process (e.g., purging/discharging as waste, directing to a subsequent unit operation for further processing, etc.); and recycling a second portion of the recycle fraction to the reaction zone or feed thereto. FIG. 3 presents a diagram depicting a process in accordance with these embodiments. As referred to herein, on-path intermediates include, for example, various aldonic acids and uronic acids which upon further oxidation yield the aldaric acid. For example, the principal on-path intermediates present in the oxidation of glucose include gluconic acid, gulluronic acid, and glucuronic acid.

In various embodiments of these processes, the concentration of the oxidation reaction inhibitor in the second portion of the recycle fraction can be about 0.5 wt. % or less, about 0.3 wt. % or less, about 0.1 wt. % or less, about 0.05 wt. % or less, or about 0.01 wt. % or less. For example, the concentration of the oxidation reaction inhibitor in the second portion of the recycle fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

In various embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In various embodiments of these processes, the oxidation reactant comprises the $C_5$-$C_6$ aldose. For example, the $C_5$-$C_6$ aldose can be selected from the group consisting of arabinose, lyxose, ribose, xylose, allose, altrose, galactose, glucose, gulose, idose, mannose, talose, and mixtures thereof. In certain embodiments, the $C_5$-$C_6$ aldose comprises glucose. In some embodiments, the $C_5$-$C_6$ aldose is obtained from a carbohydrate-containing source. In these and other embodiments, the $C_5$-$C_6$ aldose is obtained from a grain crop.

In various embodiments, the oxidation reactant comprises the $C_5$-$C_6$ aldonic acid and/or lactone(s) thereof. For example, the $C_5$-$C_6$ aldonic acid can be selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof. In certain embodiments, the $C_5$-$C_6$ aldonic acid comprises gluconic acid.

In some embodiments, the oxidation reactant comprises the $C_5$-$C_6$ uronic acid and/or lactone(s) thereof. For example, the $C_5$-$C_6$ uronic acid can be selected from the group consisting of arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof. In certain embodiments, the $C_5$-$C_6$ uronic acid comprises guluronic acid.

In various embodiments of these processes, the reaction mixture comprises a $C_5$-$C_6$ aldaric acid that is selected from the group consisting of arabinaric acid, lyxaric acid, ribaric acid, xylaric acid, allaric acid, altraric acid, galactaric acid, glucaric acid, gularic acid, idaric acid, mannaric acid, talaric acid, and mixtures thereof. In certain embodiments, the reaction mixture comprises glucaric acid.

Processes for Producing Uronic Acids and/or Lactone(s) Thereof

Other embodiments are directed to processes for preparing a $C_5$-$C_6$ uronic acid (e.g., guluronic acid) and/or lactone(s) thereof. Various processes comprise feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ uronic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less. FIG. 1 presents a diagram depicting a process in accordance with these embodiments.

In various embodiments of these processes, the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Also, in some embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

Other processes for preparing a $C_5$-$C_6$ uronic acid (e.g., guluronic acid) and/or lactone(s) thereof comprise feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a separation zone to separate at least a portion of the oxidation reaction inhibitor from the mixture and form a first fraction comprising the oxidation reactant and a second fraction comprising the oxidation reaction inhibitor; feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ uronic acid and/or lactone(s) thereof. FIG. 2 presents a diagram depicting a process in accordance with these embodiments.

In various embodiments of these processes, the molar ratio of the oxidation reaction inhibitor to the oxidation reactant in the first fraction can be less than the molar ratio of the oxidation reaction inhibitor to oxidation reactant in the feed mixture. In some embodiments, the molar ratio of the oxidation reaction inhibitor to oxidation reactant in the first fraction is less than the molar ratio of the oxidation reaction inhibitor to oxidation reactant in the second fraction.

In various embodiments, the concentration of the oxidation reactant in the first fraction is about 1 wt. % or greater, about 5 wt. % or greater, about 10 wt. % or greater, about 15 wt. % or greater, or about 20 wt. % or greater. For example, the concentration of the oxidation reactant in the first fraction can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In some embodiments, the concentration of the oxidation reaction inhibitor in the first fraction can be less than the concentration of the oxidation reaction inhibitor in the second fraction. In various embodiments, the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less. For example, the concentration of the oxidation reaction inhibitor in the first fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Further processes for preparing a $C_5$-$C_6$ uronic acid (e.g., guluronic acid) and/or lactone(s) thereof comprise feeding a feed mixture comprising at least one oxidation reactant selected from the group consisting of a $C_5$-$C_6$ aldose, a $C_5$-$C_6$ aldonic acid and/or lactone(s) thereof, and mixtures thereof to a reaction zone; reacting the oxidation reactant in the presence of oxygen and an oxidation catalyst in the reaction zone to form a reaction mixture comprising (a) the $C_5$-$C_6$ uronic acid and/or lactone(s) thereof, (b) unreacted oxidation reactant(s) and/or on-path intermediate(s) thereof, and (c) an oxidation reaction inhibitor; feeding the reaction mixture to a separation zone to separate at least a portion of the $C_5$-$C_6$ uronic acid and/or lactone(s) thereof from the reaction mixture and form a product fraction comprising the $C_5$-$C_6$ uronic acid and/or lactone(s) thereof and a recycle fraction comprising the unreacted oxidation reactant(s) and/or on-path intermediate(s) thereof and the oxidation reaction inhibitor; removing a first portion of the recycle fraction from the process (e.g., purging/discharging as waste, directing to a subsequent unit operation for further processing, etc.); and recycling a second portion of the recycle fraction to the reaction zone or feed thereto. FIG. 3 presents a diagram depicting a process in accordance with these embodiments.

In various embodiments of these processes, the concentration of the oxidation reaction inhibitor in the second portion of the recycle fraction can be about 0.5 wt. % or less, about 0.3 wt. % or less, about 0.1 wt. % or less, about 0.05 wt. % or less, or about 0.01 wt. % or less. For example, the concentration of the oxidation reaction inhibitor in the second portion of the recycle fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

In various embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In various embodiments of these processes, the oxidation reactant comprises the $C_5$-$C_6$ aldose. For example, the $C_5$-$C_6$ aldose can be selected from the group consisting of arabinose, lyxose, ribose, xylose, allose, altrose, galactose, glucose, gulose, idose, mannose, talose, and mixtures thereof. In certain embodiments, the $C_5$-$C_6$ aldose comprises glucose. In some embodiments, the $C_5$-$C_6$ aldose is obtained from a carbohydrate-containing source. In these and other embodiments, the $C_5$-$C_6$ aldose is obtained from a grain crop.

In various embodiments, the oxidation reactant comprises the $C_5$-$C_6$ aldonic acid and/or lactone(s) thereof. For example, the $C_5$-$C_6$ aldonic acid can be selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof. In certain embodiments, the $C_5$-$C_6$ aldonic acid comprises gluconic acid.

In various embodiments of these processes, the reaction mixture comprises a $C_5$-$C_6$ uronic acid that is selected from the group consisting of arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof. In certain embodiments, the $C_5$-$C_6$ uronic acid comprises guluronic acid.

Processes for Producing Aldonic Acids and/or Lactone(s) Thereof

Embodiments of the present invention also include processes for producing aldonic acids and/or lactone(s). Various processes comprise feeding a feed mixture comprising (a) an oxidation reactant comprising a $C_5$-$C_6$ aldose and (b) an oxidation reaction inhibitor to a reaction zone; and reacting the oxidation reactant in the presence of oxygen and an oxidation catalyst in the reaction zone to form a reaction mixture comprising the $C_5$-$C_6$ aldonic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less. FIG. 1 presents a diagram depicting a process in accordance with these embodiments.

In various embodiments of these processes, the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Also, in some embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

Other processes for preparing a $C_5$-$C_6$ aldonic acid and/or lactone(s) thereof comprise feeding a feed mixture comprising (a) an oxidation reactant comprising a $C_5$-$C_6$ aldose and (b) an oxidation reaction inhibitor to a separation zone to separate at least a portion of the oxidation reaction inhibitor from the mixture and form a first fraction comprising the oxidation reactant and a second fraction comprising the oxidation reaction inhibitor; feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ aldonic acid and/or lactone(s) thereof. FIG. 2 presents a diagram depicting a process in accordance with these embodiments.

In various embodiments of these processes, the molar ratio of the oxidation reaction inhibitor to the oxidation reactant in the first fraction can be less than the molar ratio of the oxidation reaction inhibitor to oxidation reactant in the feed mixture. In some embodiments, the molar ratio of the oxidation reaction inhibitor to oxidation reactant in the first fraction is less than the molar ratio of the oxidation reaction inhibitor to oxidation reactant in the second fraction.

In various embodiments, the concentration of the oxidation reactant in the first fraction is about 1 wt. % or greater, about 5 wt. % or greater, about 10 wt. % or greater, about 15 wt. % or greater, or about 20 wt. % or greater. For example, the concentration of the oxidation reactant in the first fraction can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In some embodiments, the concentration of the oxidation reaction inhibitor in the first fraction can be less than the concentration of the oxidation reaction inhibitor in the second fraction. In various embodiments, the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less. For example, the concentration of the oxidation reaction inhibitor in the first fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

Further processes for preparing a $C_5$-$C_6$ aldonic acid and/or lactone(s) thereof comprise feeding a feed mixture comprising an oxidation reactant comprising a $C_5$-$C_6$ aldose to a reaction zone reacting the oxidation reactant in the presence of oxygen and an oxidation catalyst in the reaction zone to form a reaction mixture comprising (a) the $C_5$-$C_6$ aldonic acid and/or lactone(s) thereof, (b) unreacted oxidation reactant(s) and/or on-path intermediate(s) thereof, and (c) an oxidation reaction inhibitor; feeding the reaction mixture to a separation zone to separate at least a portion of the $C_5$-$C_6$ aldonic acid and/or lactone(s) thereof from the reaction mixture and form a product fraction comprising the $C_5$-$C_6$ aldonic acid and/or lactone(s) thereof and a recycle fraction comprising the unreacted oxidation reactant(s) and/or on-path intermediate(s) thereof and the oxidation reaction inhibitor; removing a first portion of the recycle fraction from the process (e.g., purging/discharging as waste, directing to a subsequent unit operation for further processing, etc.); and recycling a second portion of the recycle fraction to the reaction zone or feed thereto. FIG. 3 presents a diagram depicting a process in accordance with these embodiments.

In various embodiments of these processes, the concentration of the oxidation reaction inhibitor in the second portion of the recycle fraction can be about 0.5 wt. % or less, about 0.3 wt. % or less, about 0.1 wt. % or less, about 0.05 wt. % or less, or about 0.01 wt. % or less. For example, the concentration of the oxidation reaction inhibitor in the second portion of the recycle fraction can be from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

In various embodiments, the concentration of the oxidation reactant in the feed mixture is about 1 wt. % or greater, about 5 wt. % or greater, about 10 wt. % or greater, about 15 wt. % or greater, or about 20 wt. % or greater. For example, the concentration of the oxidation reactant in the feed mixture can be from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

In various embodiments of these processes, the $C_5$-$C_6$ aldose is selected from the group consisting of arabinose, lyxose, ribose, xylose, allose, altrose, galactose, glucose, gulose, idose, mannose, talose, and mixtures thereof. In certain embodiments, the $C_5$-$C_6$ aldose comprises glucose. In some embodiments, the $C_5$-$C_6$ aldose is obtained from a carbohydrate-containing source. In these and other embodiments, the $C_5$-$C_6$ aldose is obtained from a grain crop.

In various embodiments, the reaction mixture comprises a $C_5$-$C_6$ aldonic acid that is selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof. In certain embodiments, the $C_5$-$C_6$ aldonic acid comprises gluconic acid.

Additional Processes and Process Features

Various processes described herein comprise or can further comprise a separation zone. In some embodiments, the separation zone can comprise a chromatographic separation stage. In various embodiments, the chromatographic separation stage comprises a separation media. In certain embodiments, the separation media comprises an amphoteric and/or anionic chromatography resin.

As noted, pH mediation typically results in lower product yields due to the over conversion of aldaric acid to other derivatives. Accordingly, in various embodiments, the processes described herein can be conducted in the absence of added base. For example, wherein the pH of the reaction mixture is not controlled or increased by the addition of base and/or wherein base is not fed to the reaction zone. In further embodiments, the processes can be conducted wherein the pH of the reaction mixture is not controlled or increased by the addition of base. In some embodiments, the processes can be conducted wherein the reaction mixture is free or essentially free of salt-forming cations.

In various embodiments, the pH of the reaction mixture(s) of the processes described herein, as measured at 20° C., is about 7 or less, about 6.5 or less, about 6 or less, about 5 or less, about 4 or less, about 3 or less, or about 2 or less. For example, the pH of the reaction mixture(s) of the processes described herein, as measured at 20° C., can be from about 1 to about 7, from about 1 to about 6, from about 1 to about 5, from about 1 to about 4, from about 1.5 to about 7, from about 1.5 to about 6, from about 1.5 to about 5, from about 1.5 to about 4, from about 2 to about 7, from about 2 to about 6, from about 2 to about 5, or from about 2 to about 4. In some embodiments, the reaction mixture(s) can reach a minimum pH measured at 20° C. of about 4 or less, about 3 or less, or about 2 or less.

In certain embodiments, the reaction zone is heated to a temperature of about 60° C. or greater, about 70° C. or greater, or about 80° C. or greater. For example, the reaction zone can be heated to a temperature of from about 60° C. to about 150° C., from about 70° C. to about 150° C., from about 80° C. to about 150° C., from about 60° C. to about 125° C., from about 70° C. to about 125° C., from about 80° C. to about 125° C., from about 60° C. to about 100° C., from about 70° C. to about 100° C., or from about 80° C. to about 100° C.

In certain embodiments, the oxygen is supplied to the reaction zone as an oxygen-containing gaseous mixture. For example, in some embodiments, the oxygen is supplied to the reaction zone as air, oxygen-enriched air, a mixture comprising oxygen, a mixture comprising at least about 40 or 50 vol. % oxygen, a mixture comprising oxygen and nitrogen (e.g., about 50:50 mixture by volume), or substantially pure oxygen (at least 99 vol. % oxygen). In various embodiments, the oxygen is supplied to the reaction zone as a mixture having an oxygen concentration of about 0.5 vol. % or greater, about 1 vol. % or greater, about 5 vol. % or greater, or about 10 vol. % or greater. For example, in various embodiments, the oxygen is supplied to the reaction zone as a mixture having an oxygen concentration of from about 0.5 vol. % to about 20 vol. %, from about 0.5 vol. % to about 15 vol. %, from about 0.5 vol. % to about 10 vol. %, from about 0.5 vol. % to about 5 vol. %, from about 1 vol. % to about 20 vol. %, from about 1 vol. % to about 15 vol. %, from about 1 vol. % to about 10 vol. %, from about 1 vol. % to about 5 vol. %, from about 5 vol. % to about 20 vol. %, from about 5 vol. % to about 15 vol. %, or from about 5 vol. % to about 10 vol. %. In certain embodiments, the oxygen is supplied to the reaction zone as a mixture having an oxygen concentration of about 10 vol. % or less, about 5 vol. % or less, about 4 vol. % or less, about 3 vol. % or less, about 2 vol. % or less, about 1 vol. % or less, or about 0.5 vol. % or less. For example, from about 10 vol. % to about 0.5 vol. %, from about 5 vol. % to about 0.5 vol. %, from about 4 vol. % to about 0.5 vol. %, from about 3 vol. % to about 0.5 vol. %, from about 2 vol. % to about 0.5 vol. %, or from about 1 vol. % to about 0.5 vol. %.

In various embodiments, the partial pressure of oxygen in the reaction zone is about 2 psig or greater, about 25 psig or greater, about 50 psig or greater, or about 100 psig or greater. For example, the partial pressure of oxygen in the reaction zone can be from about 2 psig to about 2000 psig, from about 50 psig to about 2000 psig, or from about 100 psig to about 2000 psig.

Generally, the processes described herein are catalytic processes, but do not require the application of electric current. Accordingly, in various embodiments, the processes described herein are not electrochemical processes and/or do not comprise applying an electric current to the reaction mixture (e.g., via electrodes).

As noted, processes of the present invention can provide for enhanced product yield. In some embodiments, the yield of $C_5$-$C_6$ aldonic acid and/or lactone(s) thereof, $C_5$-$C_6$ uronic acid and/or lactone(s) thereof, and/or $C_5$-$C_6$ aldaric acid and/or lactone(s) thereof is about 50% or greater, about 55% or greater, about 60% or greater, about 65% or greater, about 70% or greater, or about 75% or greater. For example, the yield of $C_5$-$C_6$ aldonic acid and/or lactone(s) thereof, $C_5$-$C_6$ uronic acid and/or lactone(s) thereof, and/or $C_5$-$C_6$ aldaric acid and/or lactone(s) thereof can be from about 50% to about 85%, from about 50% to about 80%, from about 50% to about 75%, from about 50% to about 70%, from about 50% to about 65%, from about 60% to about 85%, from about 60% to about 80%, from about 60% to about 75%, from about 60% to about 70%, from about 65% to about 85%, from about 65% to about 80%, from about 65% to about 75%, or from about 65% to about 70%.

In embodiments where the $C_5$-$C_6$ aldaric acid and/or lactone(s) comprises glucaric acid and/or lactone(s) thereof, the yield of glucaric acid and/or lactone(s) thereof can be about 50% or greater, about 55% or greater, about 60% or greater, about 65% or greater, about 70% or greater, or about 75% or greater. In various embodiments, the yield of glucaric acid and/or lactone(s) thereof can be from about 50% to about 85%, from about 50% to about 80%, from about 50% to about 75%, from about 50% to about 70%, from about 50% to about 65%, from about 60% to about 85%, from about 60% to about 80%, from about 60% to about 75%, from about 60% to about 70%, from about 65% to about 85%, from about 65% to about 80%, from about 65% to about 75%, or from about 65% to about 70%.

Also, processes of the present invention can provide for stable yield even at high reactor throughput. In certain embodiments, the liquid hourly space velocity (LHSV) of the reaction zone is about 0.2 hr$^{-1}$ or greater, about 0.5 hr$^{-1}$ or greater, about 1 hr$^{-1}$ or greater, about 1.5 hr$^{-1}$ or greater, about 2 hr$^{-1}$ or greater, about 5 hr$^{-1}$ or greater, or about 10 hr$^{-1}$ or greater. For example, the LHSV of the reaction zone can be from about 0.2 hr$^{-1}$ to about 50 hr$^{-1}$, from about 0.5 hr$^{-1}$ to about 50 hr$^{-1}$, from about 1 hr$^{-1}$ to about 50 hr$^{-1}$, from about 2 hr$^{-1}$ to about 50 hr$^{-1}$, from about 5 hr$^{-1}$ to about 50 hr$^{-1}$, from about 10 hr$^{-1}$ to about 50 hr$^{-1}$, from about 0.2 hr$^{-1}$ to about 10 hr$^{-1}$, from about 0.5 hr$^{-1}$ to about 10 hr$^{-1}$, from about 1 hr$^{-1}$ to about 10 hr$^{-1}$, from about 2 hr$^{-1}$ to about 10 hr$^{-1}$, or from about 5 hr$^{-1}$ to about 10 hr$^{-1}$. In some embodiments, product yields (e.g., yields of $C_5$-$C_6$ aldaric acids, for example glucaric acid, and/or lactone(s) thereof) of at least about 60%, at least about 65%, at least about 70%, or at least about 75% can be achieved at or within the aforementioned LHSV ranges.

The reaction mixture and/or feed mixture can include a solvent. Solvents suitable for the oxidation reaction include, for example, water or aqueous solutions of a carboxylic acid (e.g., acetic acid).

In general, the reaction zone can include one or more batch, semi-batch, or continuous reactor designs using fixed bed reactors, trickle bed reactors, slurry phase reactors, moving bed reactors, or any other design that allows for catalytic reactions, particularly heterogeneous catalytic reactions. Examples of reactors can be seen in *Chemical Process Equipment—Selection and Design*, Couper et al., Elsevier 1990, which is incorporated herein by reference. In various processes described herein, the reaction zone comprises one or more trickle bed reactors. It should be understood that reactants, oxygen, any solvent, and the catalysts may be introduced into a suitable reactor separately or in various combinations.

Aldaric, aldonic, and uronic acids and/or lactone(s) thereof produced in accordance with the processes described herein can be converted to various other derivatives, such as salts, esters, ketones, and lactones. Methods to convert carboxylic acids to such derivatives are known in the art, see, for example, Wade, *Organic Chemistry* 3$^{rd}$ ed., Prentice Hall 1995.

Catalyst(s)

As noted, the processes described herein include the use of an oxidation catalyst. The oxidation catalyst referred to herein can comprise one or more catalyst(s) effective for the oxidation reaction(s).

Generally, the oxidation catalyst comprises a catalytically active phase. In various embodiments, the catalytically active phase comprises one or more noble metals. For example, the catalytically active phase can comprise platinum and/or gold.

As noted, the concentration of one or more the oxidation reaction inhibitor(s) is believed to be related to the degree of inhibition of the oxidation reaction. Further, without being bound by theory, the molar ratio of the oxidation reaction inhibitor to the catalytically active phase can be another factor affecting the degree of inhibition of the oxidation reaction. Accordingly, in certain embodiments, the molar ratio of the oxidation reaction inhibitor to the catalytically active phase is about 50:1 or less, about 40:1 or less, about 30:1 or less, about 20:1 or less, about 10:1 or less, about 5:1 or less, about 1:1 or less, or about 0.1:1 or less. For example, the molar ratio of the oxidation reaction inhibitor to the catalytically active phase can be from about 0.001:1 to about 50:1, from about 0.001:1 to about 20:1, from about 0.001:1 to about 10:1, from about 0.001:1 to about 1:1, from about 0.001:1 to about 0.1:1, from about 0.001:1 to about 0.01:1, from about 0.01:1 to about 50:1, from about 0.01:1 to about 20:1, from about 0.01:1 to about 10:1, from about 0.01:1 to about 1:1, from about 0.01:1 to about 0.1:1, from about 0.1:1 to about 50:1, from about 0.1:1 to about 20:1, from about 0.1:1 to about 10:1, from about 0.1:1 to about 1:1, from about 1:1 to about 50:1, from about 1:1 to about 20:1, or from about 1:1 to about 10:1.

In various embodiments, the oxidation catalyst has a loading of the catalytically active phase of about 10 wt. % or less, about 7.5 wt. % or less, about 5 wt. % or less, about 4 wt. % or less, about 2 wt. % or less, or about 1 wt. % or less. In other embodiments, the oxidation catalyst has a loading of the catalytically active phase of about 0.1 wt. % or greater, about 0.25 wt. % or greater, about 0.5 wt. % or greater, about 0.75 wt. % or greater, or about 1 wt. % or greater. For example, in some embodiments, the oxidation catalyst has a loading of the catalytically active phase of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 1 wt. % to about 10 wt. %, from about 1 wt. % to about 7.5 wt. %, from about 1 wt. % to about 5 wt. %, from about 1 wt. % to about 4 wt. %, or from about 1 wt. % to about 3 wt. %.

In various embodiments, the oxidation catalyst is a heterogeneous catalyst. In some embodiments, the oxidation catalyst comprises a catalyst support. For example, the support of the oxidation catalyst can comprise a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof. In certain embodiments, the support of the oxidation catalyst comprises carbon, titania, zirconia, and combinations thereof. In other embodiments, the support of the oxidation catalyst comprises zirconia, doped zirconia, doped zirconia-metal composite, doped zirconia-metal oxide composite, titania, doped titania, doped titania-metal composite, doped titania-metal oxide composite, and mixtures thereof. In further embodiments, the support of the oxidation catalyst comprises at least one carbon material selected from the group consisting of graphite, carbon black, activated carbon and combinations thereof. In certain embodiments, the support of the oxidation catalyst comprises carbon black. Various carbon supports and methods of preparing these supports and catalyst compositions are described in U.S. Pat. No. 9,682,368 and U.S. Patent Application Publication Nos. 2017/0120223 and 2017/0120219, each of which are incorporated herein by reference.

In various embodiments, the oxidation catalyst can have a BET specific surface area that is at least about 5 m$^2$/g, at least about 100 m$^2$/g, at least about 200 m$^2$/g, at least about 500 m$^2$/g, at least about 1,000 m$^2$/g, at least about 1,500 m$^2$/g, or at least about 2,000 m$^2$/g. For example, the oxidation catalyst can have a BET specific surface area that is from about 5 m$^2$/g to about 2,500 m$^2$/g, from about 5 m$^2$/g to about 2,000 m$^2$/g, from about 5 m$^2$/g to about 1,500 m$^2$/g, from about 5 m$^2$/g to about 1,000 m$^2$/g, from about 5 m$^2$/g to about 500 m$^2$/g, from about 5 m$^2$/g to about 200 m$^2$/g, from about 100 m$^2$/g to about 2,500 m$^2$/g, from about 100 m$^2$/g to about 2,000 m$^2$/g, from about 100 m$^2$/g to about 1,500 m$^2$/g, from about 100 m$^2$/g to about 1,000 m$^2$/g, from about 100 m$^2$/g to about 500 m$^2$/g, or from about 100 m$^2$/g to about 200 m$^2$/g.

In certain embodiments, the oxidation catalyst can include two or more different catalysts such as a first catalyst and a second catalyst, wherein the first catalyst and second catalyst are different. In processes for preparing an aldaric acid and/or lactone(s) thereof and/or intermediates thereof by the catalytic oxidation of an aldose, aldonic acid and/or lactone(s) thereof, and/or uronic acid and/or lactone(s) thereof, it has been surprisingly discovered that employing at least two different catalysts provides for enhanced product yields (e.g., aldaric acid yields) even over prolonged operation. It is theorized that by employing at least two different catalysts that some of the inhibiting factors that are expected to limit total yield are reduced or avoided. In particular, it has been discovered that a first catalyst comprising platinum and a second catalyst comprising gold are especially effective for the catalytic oxidation of a $C_5$-$C_6$ aldose, $C_5$-$C_6$ uronic acid and/or lactone(s) thereof, and $C_5$-$C_6$ aldonic acid and/or lactone(s) thereof to the corresponding aldaric acid and/or lactone(s) thereof or intermediates thereof. This enhanced yield can be further improved where the presence of oxidation reaction inhibitors in the feed or reactions mixture(s) is reduced or limited, for example, about 0.5 wt. % or less, about 0.1 wt. % or less, about 0.05 wt. % or less, or about 0.01 wt. % or less.

As noted, in various embodiments, the first catalyst comprises platinum. This catalyst has been found to be particularly useful for the oxidation of an aldonic acid and/or lactone(s) thereof (e.g., gluconic aid) to a uronic acid and/or lactone(s) thereof (e.g., guluronic acid). In some embodiments, the first catalyst has a platinum loading of about 10 wt. % or less, about 7.5 wt. % or less, about 5 wt. % or less, about 4 wt. % or less, about 2 wt. % or less, or about 1 wt. % or less. In these and other embodiments, the first catalyst has a platinum loading of about 0.1 wt. % or greater, about 0.25 wt. % or greater, about 0.5 wt. % or greater, about 0.75 wt. % or greater, or about 1 wt. % or greater. For example, in various embodiments, the first catalyst has a platinum loading of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 1 wt. % to about 10 wt. %, from about 1 wt. % to about 7.5 wt. %, from about 1 wt. % to about 5 wt. %, from about 1 wt. % to about 4 wt. %, or from about 1 wt. % to about 3 wt. %.

In some embodiments, the first catalyst comprises a catalytically active phase where platinum can constitute a significant portion thereof. For example, in some embodiments, platinum constitutes about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the catalytically active phase of the first catalyst. In certain embodiments, platinum constitutes from about 20 wt. % to about 99 wt. %, from about 30 wt. % to about 99 wt. %, from about 40 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 20 wt. % to about 95 wt. %, from about 30 wt. % to about 95 wt. %, from about 40 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 90 wt. % to about 95 wt. %, from about 20 wt. % to about 90 wt. %, from about 30 wt. % to about 90 wt. %, from about 40 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the catalytically active phase of the first catalyst.

In various embodiments, the first catalyst is a heterogeneous catalyst. In some embodiments, the first catalyst can comprise a catalyst support. For example, the support of the first catalyst can comprise a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof. In some embodiments, the support of the first catalyst comprises a material comprising carbon, alumina, silica, titania, zirconia, and combinations thereof. In further embodiments, the support of the first catalyst comprises at least one carbon material selected from the group consisting of graphite, carbon black, activated carbon and combinations thereof (e.g., a carbon black support as noted herein). In certain embodiments, the support of the first catalyst comprises zirconia, doped zirconia, doped zirconia-metal composite, doped zirconia-metal oxide composite, titania, doped titania, doped titania-metal composite, doped titania-metal oxide composite, and mixtures thereof. In various embodiments, the support of the first catalyst comprises titania. In certain embodiments, the support of the first catalyst is not the same as the support of the first catalyst.

In various embodiments, the first catalyst can have a BET specific surface area that is at least about 5 $m^2$/g, at least about 100 $m^2$/g, at least about 200 $m^2$/g, at least about 500 $m^2$/g, at least about 1,000 $m^2$/g, at least about 1,500 $m^2$/g, or at least about 2,000 $m^2$/g. For example, the first catalyst can have a BET specific surface area that is from about 5 $m^2$/g to about 2,500 $m^2$/g, from about 5 $m^2$/g to about 2,000 $m^2$/g, from about 5 $m^2$/g to about 1,500 $m^2$/g, from about 5 $m^2$/g to about 1,000 $m^2$/g, from about 5 $m^2$/g to about 500 $m^2$/g, from about 5 $m^2$/g to about 200 $m^2$/g, from about 100 $m^2$/g to about 2,500 $m^2$/g, from about 100 $m^2$/g to about 2,000 $m^2$/g, from about 100 $m^2$/g to about 1,500 $m^2$/g, from about 100 $m^2$/g to about 1,000 $m^2$/g, from about 100 $m^2$/g to about 500 $m^2$/g, or from about 100 $m^2$/g to about 200 $m^2$/g.

As noted, in various embodiments, the oxidation catalyst can comprise a second catalyst comprising gold. This catalyst has been found to be particularly useful for the oxidation of an aldose to an aldonic acid and the oxidation of a uronic acid and/or lactone(s) thereof (e.g., guluronic aid) to an aldaric acid and/or lactone(s) thereof (e.g., glucaric acid).

In some embodiments, the oxidation catalyst comprises a second catalyst that has a gold loading of about 10 wt. % or less, about 7.5 wt. % or less, about 5 wt. % or less, about 4 wt. % or less, about 2 wt. % or less, or about 1 wt. % or less. In these and other embodiments, the second catalyst has a gold loading of about 0.1 wt. % or greater, about 0.25 wt. % or greater, about 0.5 wt. % or greater, about 0.75 wt. % or greater, or about 1 wt. % or greater. For example, in various embodiments, the second catalyst has a gold loading of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.1 wt. % to about 3 wt. %, from about 0.1 wt. % to about 2 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 0.5 wt. % to about 3 wt. %, from about 0.5 wt. % to about 2 wt. %, from about 1 wt. % to about 10 wt. %, from about 1 wt. % to about 7.5 wt. %, from about 1 wt. % to about 5 wt. %, from about 1 wt. % to about 4 wt. %, from about 1 wt. % to about 3 wt. %, or from about 1 wt. % to about 2 wt. %.

In various embodiments, the second catalyst comprises a catalytically active phase where gold can constitute a significant portion of the catalytically active phase. For example, in some embodiments, gold constitutes about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the catalytically active phase of the second catalyst. In certain embodiments, gold constitutes from about 20 wt. % to about 99 wt. %, from about 30 wt. % to about 99 wt. %, from about 40 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 20 wt. % to about 95 wt. %, from about 30 wt. % to about 95 wt. %, from about 40 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 20 wt. % to about 90 wt. %, from about 30 wt. % to about 90 wt. %, from about 40 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the catalytically active phase of the second catalyst.

In various embodiments, the second catalyst is a heterogeneous catalyst. In some embodiments, the second catalyst can comprise a catalyst support. For example, the support of the second catalyst can comprise a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof. In some embodiments, the support of the second catalyst comprises a material comprising carbon, alumina, silica, titania, zirconia, and combinations thereof. In further embodiments, the support of the second catalyst comprises at least one carbon material selected from the group consisting of graphite, carbon black, activated carbon and combinations thereof (e.g., a carbon black support as noted herein). In certain embodiments, the support of the second catalyst comprises zirconia, doped zirconia, doped zirconia-metal composite, doped zirconia-metal oxide composite, titania, doped titania, doped titania-metal composite, doped titania-metal oxide composite, and mixtures thereof. In various embodiments, the support of the second catalyst comprises titania. In certain embodiments, the support of the second catalyst is not the same as the support of the first catalyst.

In various embodiments, the second catalyst can have a BET specific surface area that is at least about 5 m$^2$/g, at least about 100 m$^2$/g, at least about 200 m$^2$/g, at least about 500 m$^2$/g, at least about 1,000 m$^2$/g, at least about 1,500 m$^2$/g, or at least about 2,000 m$^2$/g. For example, the second catalyst can have a BET specific surface area that is from about 5 m$^2$/g to about 2,500 m$^2$/g, from about 5 m$^2$/g to about 2,000 m$^2$/g, from about 5 m$^2$/g to about 1,500 m$^2$/g, from about 5 m$^2$/g to about 1,000 m$^2$/g, from about 5 m$^2$/g to about 500 m$^2$/g, from about 5 m$^2$/g to about 200 m$^2$/g, from about 100 m$^2$/g to about 2,500 m$^2$/g, from about 100 m$^2$/g to about 2,000 m$^2$/g, from about 100 m$^2$/g to about 1,500 m$^2$/g, from about 100 m$^2$/g to about 1,000 m$^2$/g, from about 100 m$^2$/g to about 500 m$^2$/g, or from about 100 m$^2$/g to about 200 m$^2$/g.

In various process as described herein, the volumetric ratio of the total amount of first catalyst to second catalyst in the reaction zone is from about 1:10 to about 10:1, from about 1:5 to about 5:1, from about 1:3 to about 3:1, or about 1:1. In further embodiments, the weight or volumetric ratio of the total amount of first catalyst to second catalyst in the reaction zone is from about 1:10 to about 10:1, from about 1:5 to about 5:1, from about 1:3 to about 3:1, or about 1:1.

In various processes described herein, the first catalyst and second catalyst can be mixed. In other words, the reaction zone can comprise a mixture (e.g., physical mixture) of the first catalyst and second catalyst.

Figure 4:
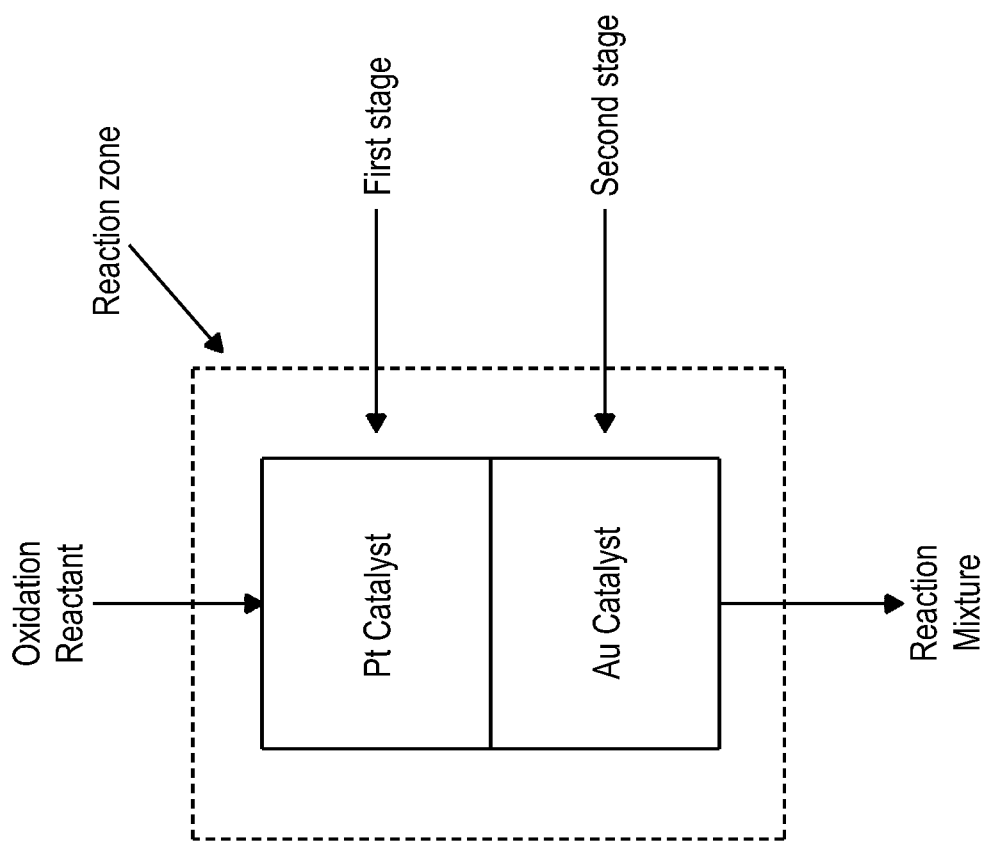
FIG. 4 presents a schematic of a two-stage reaction zone.

Further, in various processes described herein, the first catalyst and second catalyst can be staged or a combination of mixed and staged. For example, the reaction zone can comprise a first stage comprising the first catalyst and a second stage comprising the second catalyst. See FIG. 4, which is a schematic of a two-stage reaction zone.

In various embodiments comprising a first stage and/or a second stage, the first stage can comprise a mixture of the first catalyst and the second catalyst. In some embodiments, in the first stage, the weight or volume of the first catalyst can be greater than the weight or volume of the second catalyst. For instance, in various embodiments, the first stage comprises a mixture of the first catalyst and the second catalyst and the weight or volumetric ratio of the first catalyst to the second catalyst is about 2:1 or greater, about 3:1 or greater, or about 4:1 or greater. In some embodiments, the first stage comprises a mixture of the first catalyst and the second catalyst and the weight or volumetric ratio of the first catalyst to the second catalyst can be from about 2:1 to about 10:1, from about 2:1 to about 5:1, from about 3:1 to about 10:1, or from about 3:1 to about 5:1.

In embodiments comprising a first stage and a second stage, the second stage can comprise a mixture of the first catalyst and the second catalyst. In some embodiments, the weight or volume of the second catalyst can be greater than the weight or volume of the first catalyst. For instance, in various embodiments, the second stage comprises a mixture of the first catalyst and the second catalyst and the weight or volumetric ratio of the second catalyst to the first catalyst is about 2:1 or greater, about 3:1 or greater, or about 4:1 or greater. For example, the second stage comprises a mixture of the first catalyst and the second catalyst and the weight or volumetric ratio of the second catalyst to the first catalyst can be from about 2:1 to about 10:1, from about 2:1 to about 5:1, from about 3:1 to about 10:1, or from about 3:1 to about 5:1.

Figure 5:
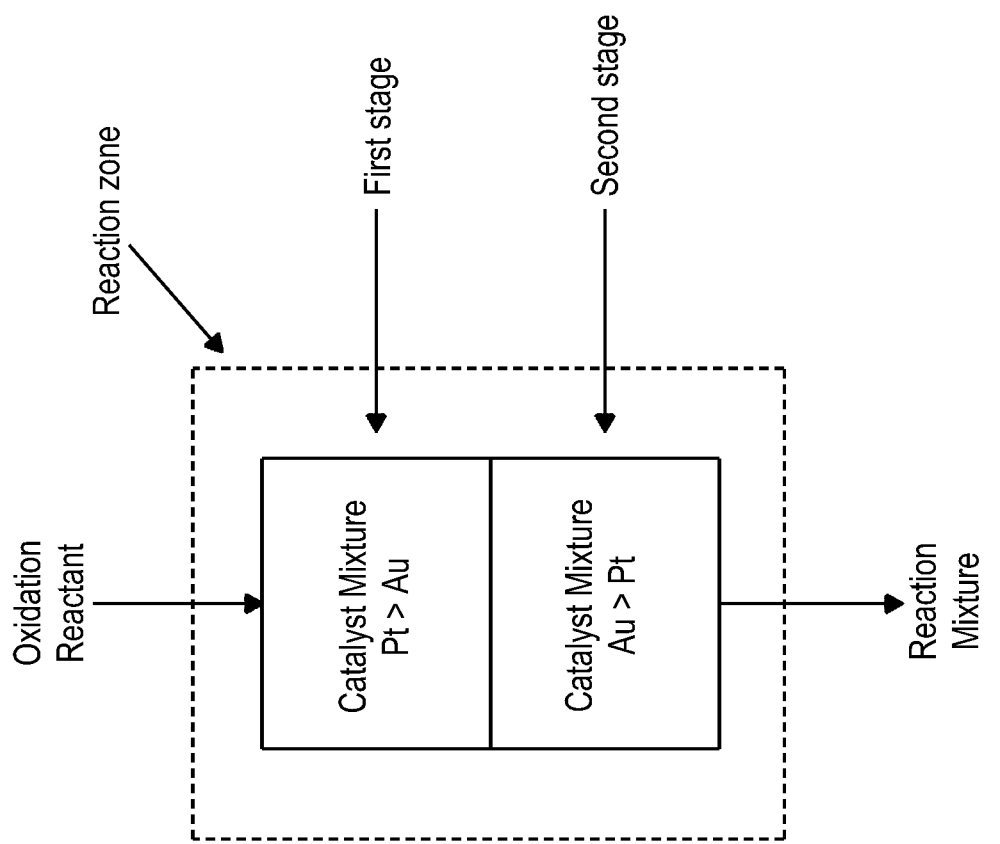
FIG. 5 depicts a schematic of a two-stage reaction zone comprising different catalyst mixtures.

In various embodiments, the first stage and second stage comprise a mixture of the first catalyst and the second catalyst. The stages can comprise different mixtures of the first and second catalyst, including the mixtures note above. FIG. 5 depicts a schematic of a two-stage reaction zone comprising different catalyst mixtures.

Figure 6:
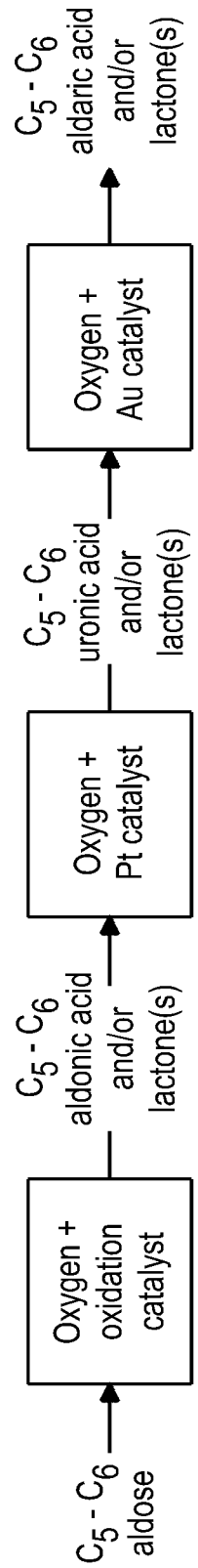
FIG. 6 depicts a diagram showing steps of an oxidation process for preparing a $C_5$-$C_6$ aldaric acid and/or lactone(s) thereof from a $C_5$-$C_6$ aldose.

As noted, various processes described herein can further include the step of reacting an aldose in the presence of oxygen and an oxidation catalyst to form the aldonic acid and/or lactone(s) thereof. In these embodiments, the oxidation catalyst, first catalyst, and second catalyst can be staged as well. For example, in some embodiments, the reaction zone can comprise an initial oxidation stage comprising the oxidation catalyst, a first stage comprising the first catalyst, and a second stage comprising the second catalyst. One example of this process is shown in FIG. 6.

When a catalyst support is used, the metals (e.g., platinum and gold) may be deposited on the catalyst supports using procedures known in the art including, but not limited to incipient wetness, ion-exchange, deposition-precipitation, and vacuum impregnation.

Processes for Analyzing and Upgrading a Feed Mixture

Various aspects of the present invention are directed to processes for analyzing and/or upgrading a feed mixture. Prior to introducing a feed mixture to a reaction zone, a feed mixture can be analyzed for the presence of one or more oxidation reaction inhibitors (e.g., by chromatography). Accordingly, in some embodiments, a process for analyzing a feed mixture comprising at least one feed component selected from the group consisting of a $C_5$-$C_6$ aldose, a $C_5$-$C_6$ aldonic acid and/or lactone(s) thereof, a $C_5$-$C_6$ uronic acid and/or lactone(s) thereof, a $C_5$-$C_6$ aldaric acid and/or lactone(s) thereof, and mixtures thereof comprises: analyzing the feed mixture to determine the components of the feed mixture and to determine the presence of any oxidation reaction inhibitor(s). The oxidation reaction inhibitor is a compound that inhibits the oxidation of the at least one feed component selected from the group consisting of a $C_5$-$C_6$ aldose, a $C_5$-$C_6$ aldonic acid and/or lactone(s) thereof, a $C_5$-$C_6$ uronic acid and/or lactone(s) thereof, a $C_5$-$C_6$ aldaric acid and/or lactone(s) thereof, and mixtures thereof.

For a given feed mixture, the degree to which a feed mixture component inhibits an oxidation reaction may not have been determined or classified. Accordingly, in some embodiments, the process further comprises determining an oxidation inhibition factor for one or more components of the feed mixture, wherein the oxidation inhibition factor is the percentage by which a reaction performance factor is reduced at a given concentration of the oxidation reaction inhibitor. In various embodiments, the reaction performance factor is selected from the group consisting of yield of an oxidation product, selectivity to an oxidation product, catalyst efficiency, yield of one or more off-path products, and combinations thereof. Further, the oxidation inhibition factor can be determined by comparing the results of a first oxidation reaction and a second oxidation reaction where the reaction mixtures and conditions for the first oxidation reaction and second oxidation reaction are the same except that the reaction mixture of the second oxidation reaction contains a greater concentration of a component of the feed mixture that is being evaluated as an oxidation reaction inhibitor.

In evaluating whether a component of the feed mixture is an oxidation reaction inhibitor, a threshold value can be established. In some embodiments, a component of the feed mixture is an oxidation reaction inhibitor if the oxidation inhibition factor is about 5% or greater, about 10% or greater, about 20% or greater, about 30% or greater, about 40% or greater, or about 50% or greater.

Embodiments of the present invention also relate to processes for producing an upgraded feed mixture. Following analysis of the feed mixture as described herein to determine the presence of an oxidation reaction inhibitor, such process includes separating at least a portion of the oxidation reaction inhibitor from the feed mixture in a separation zone to form a first fraction comprising the upgraded feed mixture and a second fraction comprising at least a portion of the oxidation reaction inhibitor. In various embodiments, the process comprises separating at least a portion of the oxidation reaction inhibitor when the oxidation reaction inhibitor has an oxidation inhibitor factor exceeding a threshold value. For example, the threshold value can be set at about 5% or greater, about 10% or greater, about 20% or greater, about 30% or greater, about 40% or greater, or about 50% or greater.

The separation zone can include various features as described herein. For example, in some embodiments, the separation zone comprises a chromatographic separation stage. In various embodiments, the chromatographic separation stage comprises a separation media. In certain embodiments, the separation media comprises an amphoteric and/or anionic chromatography resin.

The purpose of the separation zone is to reduce the concentration of the oxidation reaction inhibitor in the upgraded feed mixture. In some embodiments, the concentration of the oxidation reaction inhibitor in the upgraded feed mixture is about 0.5 wt. % or less, about 0.3 wt. % or less, about 0.1 wt. % or less, about 0.05 wt. % or less, or about 0.01 wt. % or less. In certain embodiments, the concentration of the oxidation reaction inhibitor in the upgraded feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %. Further, in various embodiments, the concentration of the oxidation reaction inhibitor in the upgraded feed mixture is reduced by about 50 wt. % or more, by about 60 wt. % or more, by about 70 wt. % or more, by about 80 wt. % or more, or by about 90 wt. % or more as compared to the concentration in the feed mixture prior to separation.

As noted herein, specific compounds that have been identified as oxidation reaction inhibitors include glyceric acid, 3-hydroxypropionic acid, 1,3-propanediol, and mixtures thereof. Accordingly, in various embodiments, the oxidation reaction inhibitor comprises at least one component selected from the group consisting of glyceric acid, 3-hydroxypropionic acid, 1,3-propanediol, and mixtures thereof. In some embodiments, the oxidation reaction inhibitor comprises glyceric acid. In certain embodiments, the oxidation reaction inhibitor comprises 3-hydroxypropionic acid.

Having described the invention in detail, it will be apparent that modifications and variations are possible without departing from the scope of the invention defined in the appended claims.

As employed herein, the term "comprising" is to be understood to also cover the alternative in which the product/method/use in respect of which the term "comprising" is used may also "consist exclusively of" the subsequently-described elements.

As employed herein, the term "comprising" is to be understood to also cover the alternative in which the product/method/use in respect of which the term "comprising" is used may also "consist essentially of" the subsequently-described elements.

Unless stated otherwise, all synthetic processes and parameter measurements are to be understood to have been conducted at room/ambient temperature, i.e. at 21±1° C.

EXAMPLES

The following non-limiting examples are provided to further illustrate the present invention.

Example 1: Glucose to Gluconic Acid Using an Au/TiO$_2$ Catalyst

A 1 wt. % Au/TiO$_2$ catalyst was loaded in to a fixed packed bed reactor. A solution of 20 wt. % glucose in water was fed to the reactor at a liquid hourly space velocity (LHSV) of 2.0 hr$^{-1}$ and a gas flow of 50% air, 50% N$_2$ was fed co-currently at a rate of 1000 SCCM. The pressure of the system was maintained at 750 psig. The temperature of the reactor jacket was varied between 75 and 85° C.

Figure 7:
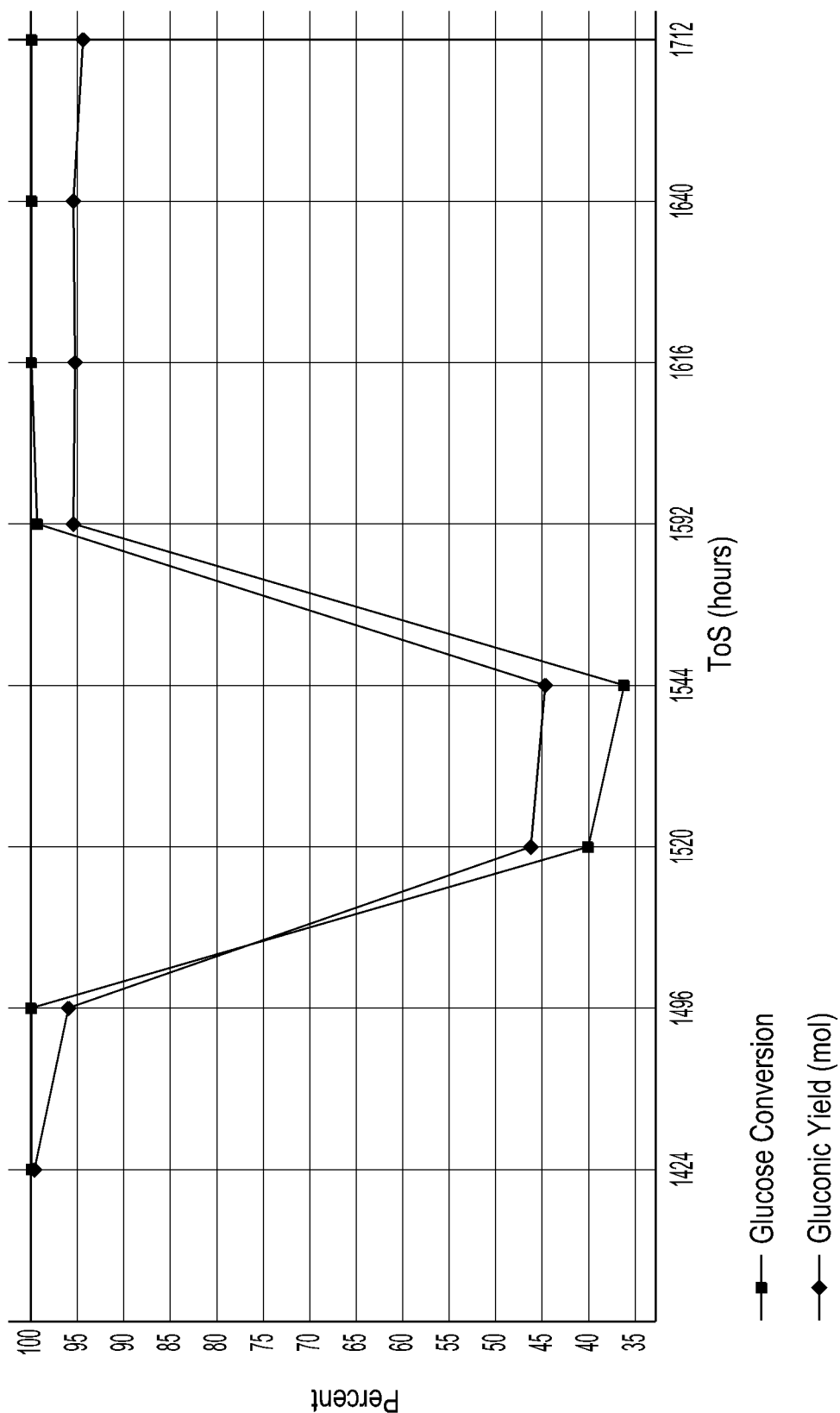
FIG. 7 reports the glucose conversion and gluconic acid yield of a process for converting glucose to gluconic acid using an Au/TiO$_2$ catalyst where glyceric acid is spiked into the glucose feed.

The reaction was run for approximately 1750 hours. Between 1520 and 1568 hours on stream, the feed was modified to include 0.8 wt. % glyceric acid with the 20 wt % glucose feed stream. As demonstrated in FIG. 7, the glucose conversion and gluconic acid yield were dramatically decreased when glyceric acid was present in the feed stream. The glucose conversion was reduced from about 100% to about 35% and the gluconic acid yield was reduced from about 98% to about 45%.

When glyceric acid was present in the feed stream the reaction temperature also dropped from a peak temperature of about 85° C. to about 77° C. This drop in temperature demonstrates that glyceric acid limits the exothermic nature of the reaction, contributing to the reduced conversion and yield.

At about 1568 hours the glyceric acid was removed from the feed stream (i.e., the feed stream was returned to a 20 wt. % glucose solution). At about 1590 hours on stream the conversion and yield returned to approximately the same levels exhibited before introduction of the glyceric acid.

Example 2: Gluconic Acid to Glucaric Acid Using a Pt/C Catalyst

Approximately 25 mg of a 4 wt. % Pt/C catalyst was loaded in to a batch reactor. 2.3 mL of a solution of 10 wt. % gluconic acid in water was introduced into the reactor. The reactor was maintained at 85° C. and was pressurized to 1800 psi with air. The reaction was conducted for 1 hour.

Seven further reactions were conducted under identical conditions, wherein various compositions were introduced into the gluconic acid feed solution to test for conversion inhibition. The inclusion of 0.08M propionic acid, 0.08M lactic acid, 0.08M glyceric acid, 0.04M glyceric acid, 0.02M tartronic acid, 0.02M tartaric acid, and 0.05M malic acid in the gluconic acid feed solution were tested.

Figure 8:
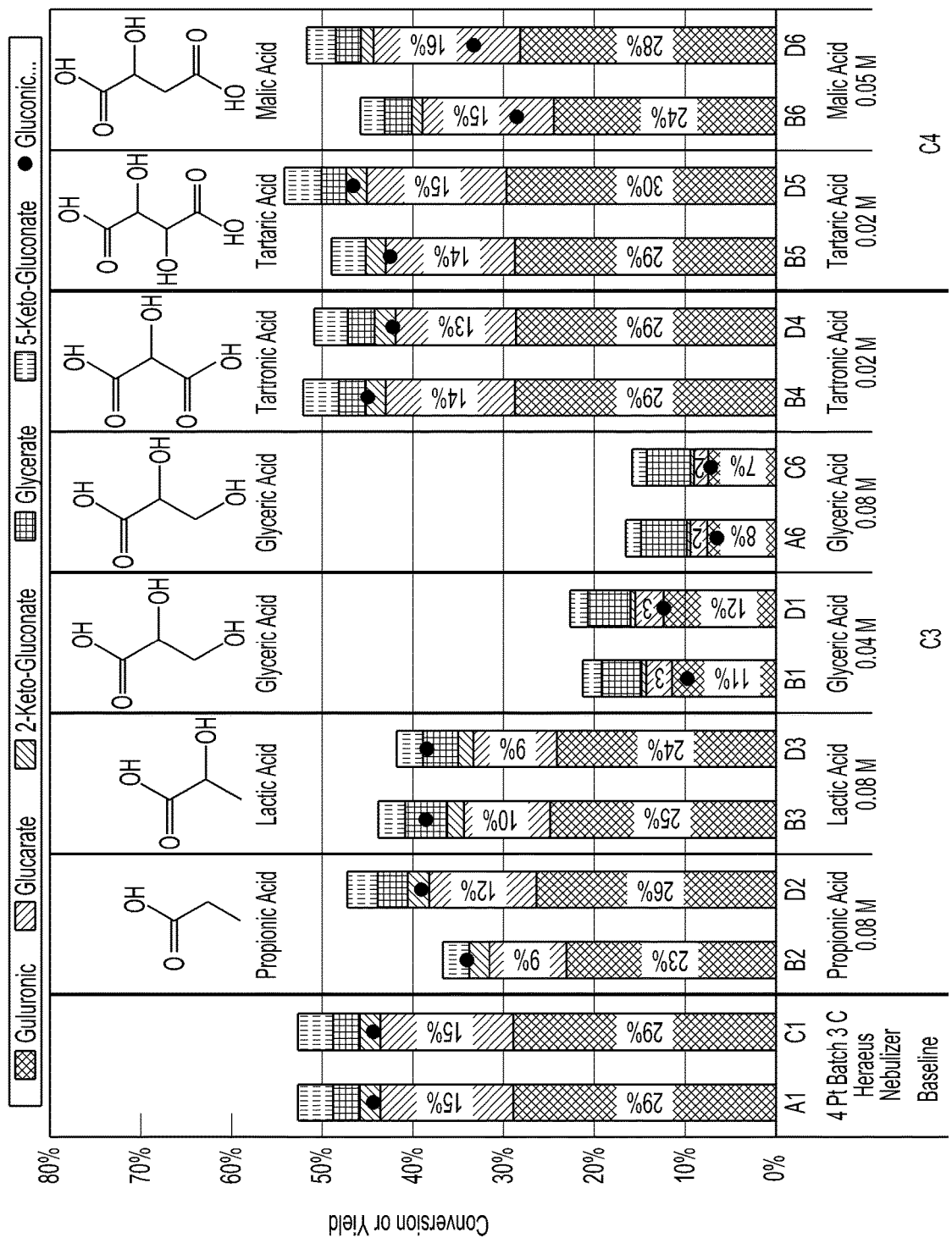
FIG. 8 reports the conversion of gluconic acid and various yields for the conversion of gluconic acid to glucaric acid using a Pt/C catalyst where potential oxidation reaction inhibitors were spiked into the feed.

FIG. 8 reports the conversion of gluconic acid and yield of guluronic acid, glucarate, 2-keto-gluconate, glycerate, and 5-keto-gluconate for each experiment. Each experiment was conducted in duplicate.

At 0.08M, or even 0.04M, glyceric acid exhibited a significant inhibitory effect on both the conversion and yields. The introduction of 0.08M propionic and 0.08M lactic acid also resulted in a noticeable inhibitory effect on the conversion and yields.

Example 3: Gluconic Acid to Glucaric Acid Using a Pt/C Catalyst

Figure 9:
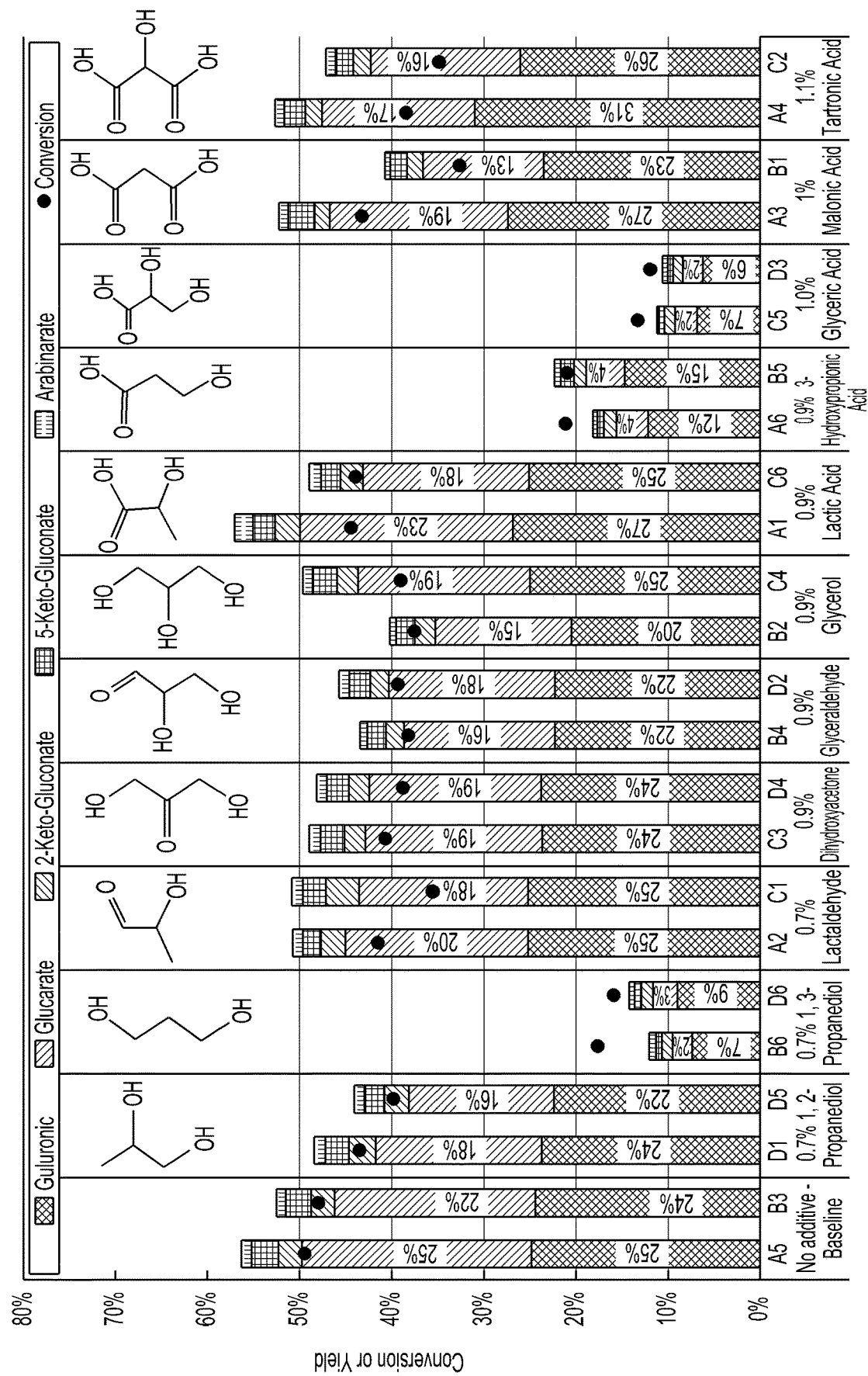
FIG. 9 reports the conversion of gluconic acid and various yields for the conversion of gluconic acid to gluconic acid using a Pt/C catalyst where potential oxidation reaction inhibitors were spiked into the feed.

A further experiment was conducted similar to Example 2. In this experiment, various 0.1M solutions were introduced into the gluconic acid feed stream to test for inhibition. The solutions tested for inhibiting effects were 0.7 wt. % 1,2-propanediol, 0.7 wt. % 1,3-propanediol, 0.7 wt. % lactaldehyde, 0.9 wt. % dihydroxyacetone, 0.9 wt. % glyceraldehyde, 0.9 wt. % glycerol, 0.9 wt. % lactic acid, 0.9 wt. % 3-hydroxypropionic acid, 1.0 wt. % glyceric acid, 1.0 wt. % malonic acid, and 1.1 wt. % tartronic acid. The reaction conditions were the same as in Example 2. FIG. 9 reports the results.

1,3-propanediol, 3-hydroxypropionic acid, and glyceric acid significantly inhibited the conversion of gluconic acid and various yields, with glyceric acid having the most pronounced effect. Moderate inhibition was also observed for several of the other tested compositions, including 1,2-propanediol, glyceraldehyde, glycerol, malonic acid, and tartronic acid.

Figure 10:
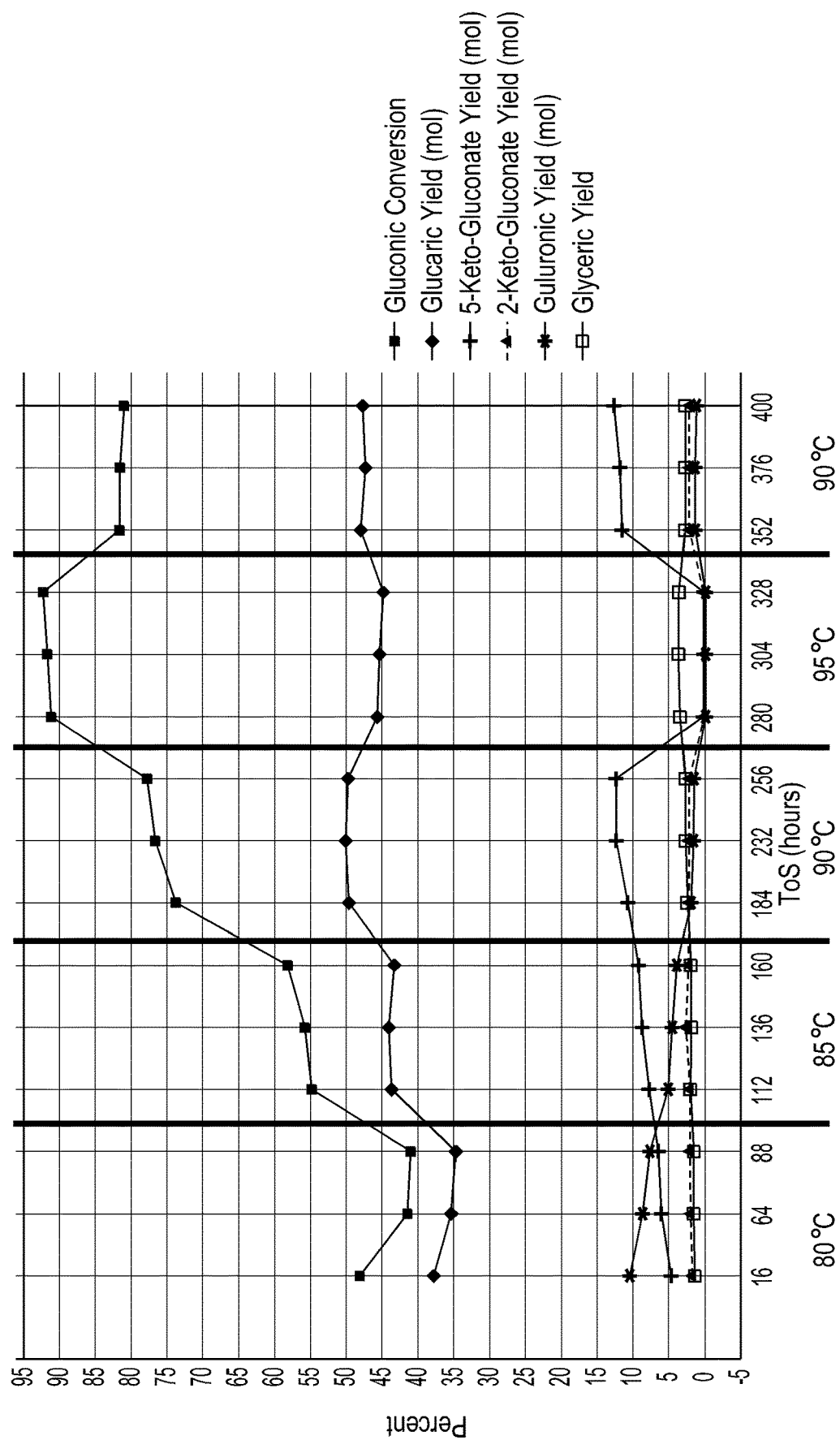
FIG. 10 reports the yield of glyceric acid during the conversion of gluconic acid to glucaric acid using a 4 wt. % Pt/C:1 wt. % Au/TiO$_2$ catalyst mixture.

Example 4: Glyceric Acid Inhibition of Gluconic Acid Conversion Using a 4 wt. % Pt/C:1 wt. % Au/TiO$_2$ Catalyst Mixture Gluconic acid was converted to glucaric acid using a physical mixture of Pt/C and Au/TiO$_2$ catalysts. A reactor bed was loaded with a physical mixture of catalysts comprising a 1:1 volumetric ratio of 4 wt. % Pt/C and 1 wt. % Au/TiO$_2$ The reactor comprised 7.325 g of the Pt/C catalyst and 14.315 g of the 1 wt. % Au/TiO$_2$ catalyst. A feed stream comprising 20.6 wt. % gluconic acid in water was introduced at a LHSV of 0.5 (0.5 mL/mL catalyst/hr) with a co-current gas flow rate of 1000 SCCM. The pressure was maintained at 1250 psig and the reactor jacket temperature was varied starting at about 80° C. and increased by 5 degrees to 95° C. for the first 340 hours of time on stream. As shown in FIG. 10 and Table 1, glyceric acid was produced during the oxidation reaction. Yield of glyceric acid increased as temperature increased, particularly at 95° C.

TABLE 1

| Time on Stream, h. | Gluconic acid conversion, % | Glucaric acid yield, % | Glyceric acid Yield, % | Glyceric acid concentration, wt % |
|---|---|---|---|---|
| 16 | 48.1 | 37.7 | 1.4 | 0.3 |
| 64 | 41.3 | 35.2 | 1.6 | 0.4 |
| 88 | 40.9 | 34.8 | 1.5 | 0.3 |
| 112 | 54.8 | 43.6 | 1.9 | 0.4 |
| 136 | 55.8 | 44.1 | 2.0 | 0.4 |
| 160 | 58.3 | 43.3 | 2.0 | 0.4 |
| 184 | 73.7 | 49.6 | 2.6 | 0.6 |
| 232 | 76.6 | 50.1 | 2.7 | 0.6 |
| 256 | 77.8 | 49.7 | 2.7 | 0.6 |
| 280 | 91.1 | 45.5 | 3.5 | 0.8 |
| 304 | 91.8 | 45.2 | 3.7 | 0.8 |
| 328 | 92.3 | 44.7 | 3.6 | 0.8 |
| 352 | 81.4 | 47.9 | 2.8 | 0.6 |
| 376 | 81.4 | 47.1 | 2.7 | 0.6 |
| 400 | 80.9 | 47.8 | 2.7 | 0.6 |

Figure 11:
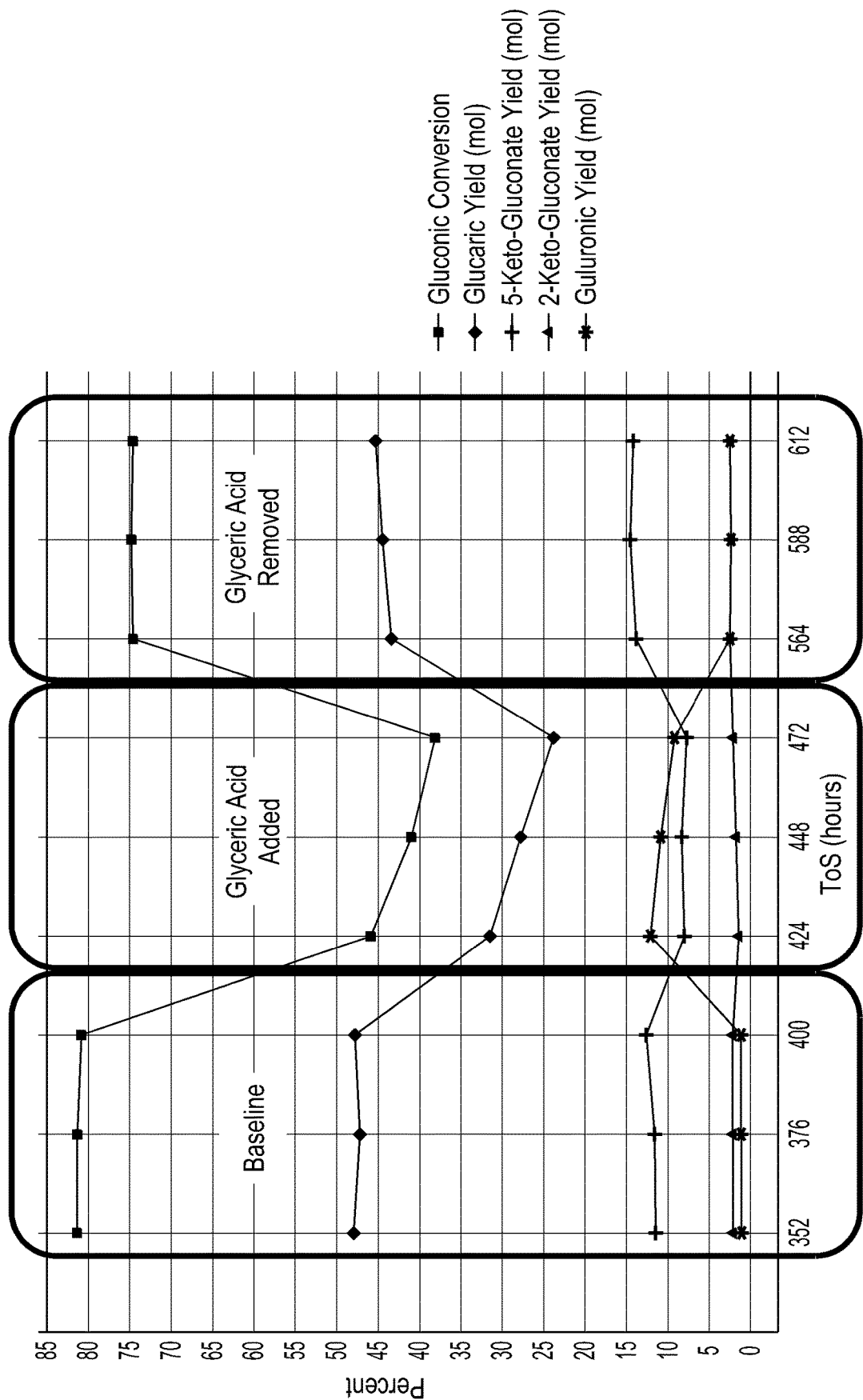
FIG. 11 reports the inhibiting effects of glyceric acid on the conversion of gluconic acid to glucaric acid using a 4 wt. % Pt/C:1 wt. % Au/TiO$_2$ catalyst mixture.

After about 340 hours, the reactor jacket was maintained at about 90° C. At about 400 hours on stream a 0.8 wt. % (0.08 M) glyceric acid composition was introduced into the gluconic acid feed. Between about 424 and 472 hours on stream, the gluconic acid conversion and various yields (e.g., glucaric acid) was significantly inhibited. Glyceric acid was removed from the feed stream after about 472 hours. After the glyceric acid was removed from the feed, the conversion increased. However, the reaction failed to return to the levels exhibited before addition of the glyceric acid. FIG. 11 reports the results of this experiment.

Example 5: Glyceric Acid Inhibition of Gluconic Acid Conversion at Various Concentrations Gluconic acid was converted to glucaric acid using a 4 wt. % Pt/C catalyst. 25 or 50 mg of catalyst was loaded into a batch reactor. 2.3 mL of a 10.8 wt. % gluconic acid in water solution was introduced into the reactor. The reactor was maintained at 85° C. and pressurized to 1800 psi with air. The reaction was conducted for 1 hour.

Various glyceric acid compositions, ranging from 0M to 0.1M, were introduced into the gluconic acid feed stream to test for reaction inhibition. These compositions were tested for both a 25 mg catalyst and 50 mg catalyst.

Figure 12:
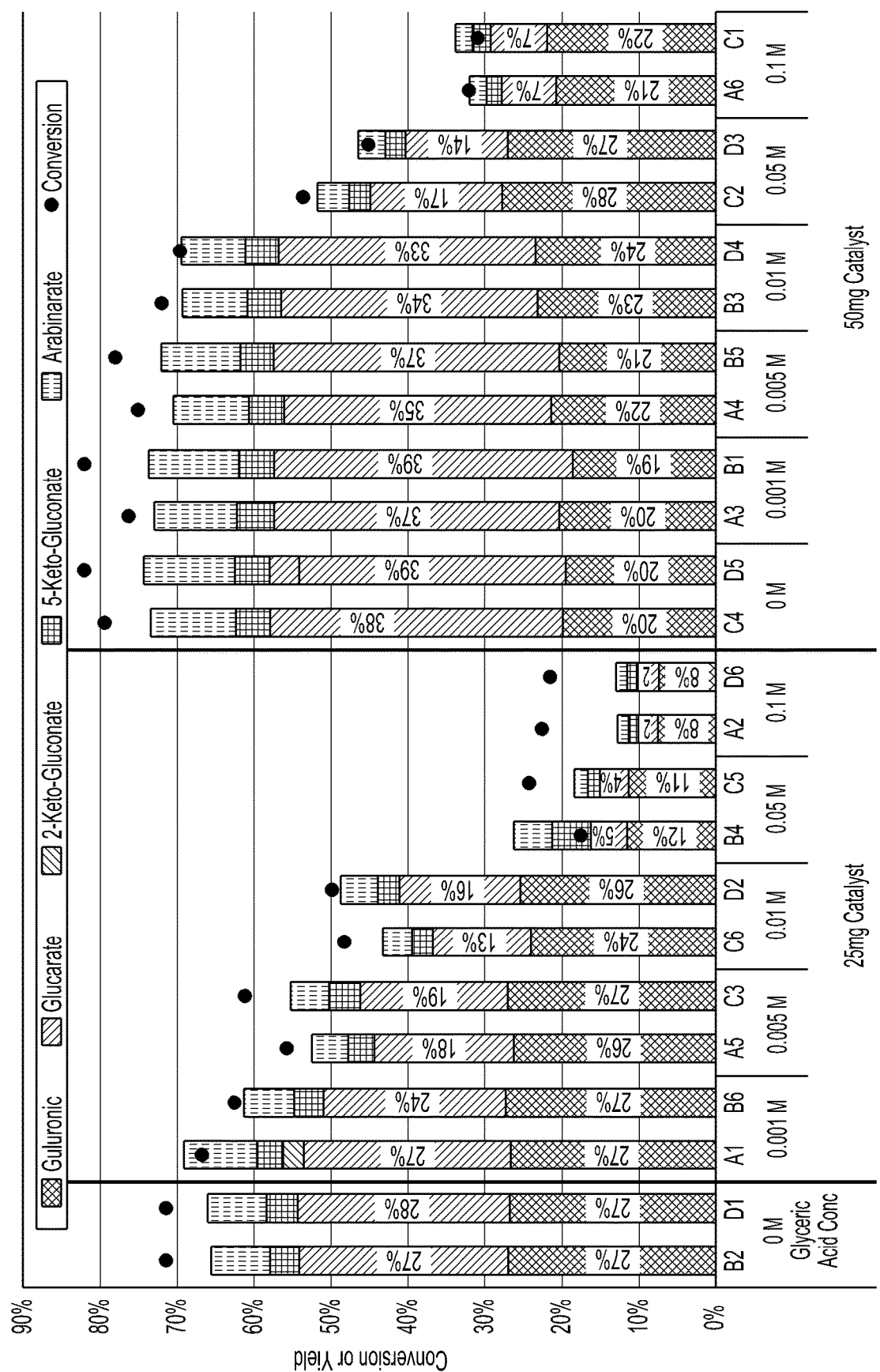
FIG. 12 reports the inhibiting effects of various concentrations of glyceric acid on the conversion of gluconic acid to glucaric acid using a 4 wt. % Pt/C:1 wt. % Au/TiO$_2$ catalyst mixture.

FIG. 12 reports the gluconic acid conversion and various yields for each glyceric acid composition. At a glyceric acid strength of 0.05M to 0.1M, the reaction was significantly inhibited, regardless of the total catalyst loaded into the reactor.

Figure 13:
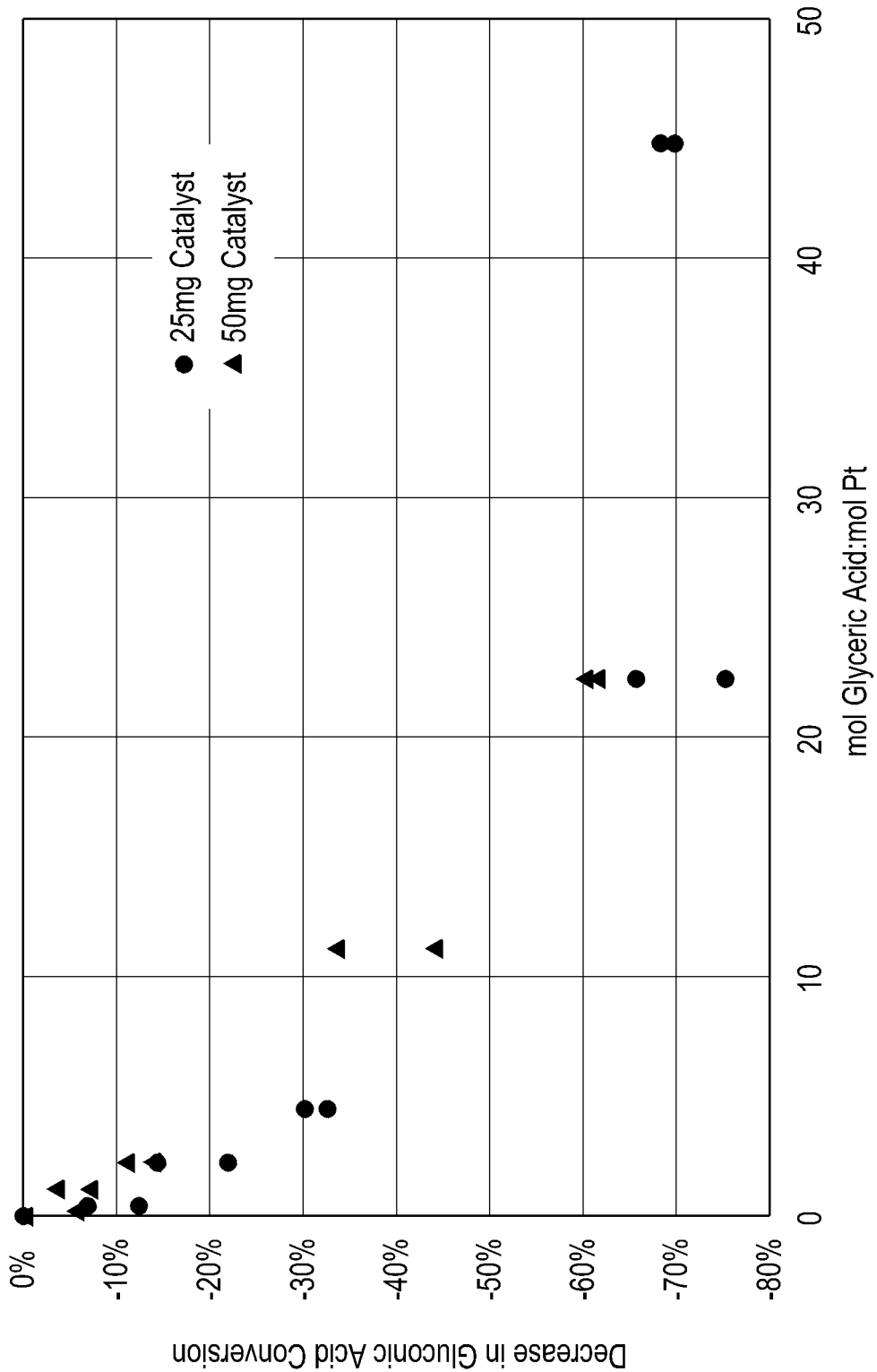
FIG. 13 reports the results of FIG. 12, comparing the decrease in gluconic acid conversion to the molar ratio of glyceric acid to platinum.

FIG. 13 reports the results of this experiment by comparing the decrease in gluconic acid conversion to the molar ratio of glyceric acid to platinum. It was observed that 60-70% of the catalyst's conversion capability is lost when the ratio approaches 20.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and processes without departing from the scope of the invention, it is intended that all matter contained in the above description and shown in the accompanying drawing(s) shall be interpreted as illustrative and not in a limiting sense.

Items:

1. A process for preparing a $C_5$-$C_6$ aldaric acid and/or lactone(s) thereof, the process comprising:

feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ aldaric acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

2. The process of item 1, wherein the concentration of the oxidation reaction inhibitor in the feed mixture is about 0.5 wt. % or less.

3. The process of any of the preceding items, wherein the concentration of the oxidation reaction inhibitor in the feed mixture is about 0.3 wt. % or less.

4. The process of any of the preceding items, wherein the concentration of the oxidation reaction inhibitor in the feed mixture is about 0.1 wt. % or less.

5. The process of any of the preceding items, wherein the concentration of the oxidation reaction inhibitor in the feed mixture is about 0.05 wt. % or less.

6. The process of any of the preceding items, wherein the concentration of the oxidation reaction inhibitor in the feed mixture is about 0.01 wt. % or less.

7. The process of item 1, wherein the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

8. The process of item 7, wherein the concentration of the oxidation reaction inhibitor in the feed mixture is from about 0.001 wt. % to about 0.5 wt. %.

9. The process of item 7, wherein the concentration of the oxidation reaction inhibitor in the feed mixture is from about 0.001 wt. % to about 0.1 wt. %.

10. The process of item 7, wherein the concentration of the oxidation reaction inhibitor in the feed mixture is from about 0.001 wt. % to about 0.05 wt. %.

11. The process of item 7, wherein the concentration of the oxidation reaction inhibitor in the feed mixture is from about 0.001 wt. % to about 0.01 wt. %.

12. The process of item 7, wherein the concentration of the oxidation reaction inhibitor in the feed mixture is from about 0.005 wt. % to about 0.5 wt. %.

13. The process of item 7, wherein the concentration of the oxidation reaction inhibitor in the feed mixture is from about 0.005 wt. % to about 0.1 wt. %.

14. The process of item 7, wherein the concentration of the oxidation reaction inhibitor in the feed mixture is from about 0.005 wt. % to about 0.05 wt. %.

15. The process of item 7, wherein the concentration of the oxidation reaction inhibitor in the feed mixture is from about 0.005 wt. % to about 0.01 wt. %.

16. The process of item 7, wherein the concentration of the oxidation reaction inhibitor in the feed mixture is from about 0.01 wt. % to about 0.5 wt. %.

17. The process of item 7, wherein the concentration of the oxidation reaction inhibitor in the feed mixture is from about 0.01 wt. % to about 0.1 wt. %.

18. The process of item 7, wherein the concentration of the oxidation reaction inhibitor in the feed mixture is from about 0.01 wt. % to about 0.05 wt. %.

19. The process of item 7, wherein the concentration of the oxidation reaction inhibitor in the feed mixture is from about 0.05 wt. % to about 0.5 wt. %.

20. The process of item 7, wherein the concentration of the oxidation reaction inhibitor in the feed mixture is from about 0.05 wt. % to about 0.1 wt. %.

21. The process of item 7, wherein the concentration of the oxidation reaction inhibitor in the feed mixture is from about 0.1 wt. % to about 0.5 wt. %.

22. The process of any one of the preceding items, wherein the concentration of the oxidation reactant in the feed mixture is about 1 wt. % or greater, about 5 wt. % or greater, about 10 wt. % or greater, about 15 wt. % or greater, or about 20 wt. % or greater.

23. The process of any one of the preceding items, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

24. The process of any one of the preceding items, wherein the concentration of the oxidation reactant in the feed mixture is from about 1 wt. % to 50 wt. %.

25. The process of any one of the preceding items, wherein the concentration of the oxidation reactant in the feed mixture is from about 1 wt. % to 25 wt. %.

26. The process of any one of the preceding items, wherein the concentration of the oxidation reactant in the feed mixture is from about 5 wt. % to 25 wt. %.

27. A process for preparing a $C_5$-$C_6$ aldaric acid and/or lactone(s) thereof, the process comprising:

feeding a feed mixture comprising (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof and (b) an oxidation reaction inhibitor to a separation zone to separate at least a portion of the oxidation reaction inhibitor from the feed mixture and form a first fraction comprising at least a portion of the oxidation reactant and a second fraction comprising at least a portion of the oxidation reaction inhibitor;

feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ aldaric acid and/or lactone(s) thereof.

28. The process of item 27, wherein the molar ratio of the oxidation reaction inhibitor to the oxidation reactant in the first fraction is less than the molar ratio of the oxidation reaction inhibitor to oxidation reactant in the feed mixture.

29. The process of item 27 or 28, wherein the molar ratio of the oxidation reaction inhibitor to oxidation reactant in the first fraction is less than the molar ratio of the oxidation reaction inhibitor to oxidation reactant in the second fraction.

30. The process of any one of items 27 to 29, wherein the concentration of the oxidation reactant in the first fraction is about 1 wt. % or greater, about 5 wt. % or greater, about 10 wt. % or greater, about 15 wt. % or greater, or about 20 wt. % or greater.

31. The process of any one of items 27 to 30, wherein the concentration of the oxidation reactant in the first fraction is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

32. The process of any one of items 27 to 31, wherein the concentration of the oxidation reactant in the first fraction is from about 1 wt. % to 50 wt. %.

33. The process of any one of items 27 to 32, wherein the concentration of the oxidation reactant in the first fraction is from about 1 wt. % to 25 wt. %.

34. The process of any one of items 27 to 33, wherein the concentration of the oxidation reactant in the first fraction is from about 5 wt. % to 25 wt. %.

35. The process of any one of items 27 to 34, wherein the concentration of the oxidation reaction inhibitor in the first fraction is less than the concentration of the oxidation reaction inhibitor in the second fraction.

36. The process of any one of items 27 to 35, wherein the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less.

37. The process of item 36, wherein the concentration of the oxidation reaction inhibitor in the first fraction is about 0.5 wt. % or less.

38. The process of item 36, wherein the concentration of the oxidation reaction inhibitor in the first fraction is about 0.3 wt. % or less.

39. The process of item 36, wherein the concentration of the oxidation reaction inhibitor in the first fraction is about 0.1 wt. % or less.

40. The process of item 36, wherein the concentration of the oxidation reaction inhibitor in the first fraction is about 0.05 wt. % or less.

41. The process of item 36, wherein the concentration of the oxidation reaction inhibitor in the first fraction is about 0.01 wt. % or less.

42. The process of any one of items 27 to 36, wherein the concentration of the oxidation reaction inhibitor in the first fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

43. The process of item 42, wherein the concentration of the oxidation reaction inhibitor in the first fraction is from about 0.001 wt. % to about 0.5 wt. %. 44. The process of item 42, wherein the concentration of the oxidation reaction inhibitor in the first fraction is from about 0.001 wt. % to about 0.1 wt. %.

45. The process of item 42, wherein the concentration of the oxidation reaction inhibitor in the first fraction is from about 0.001 wt. % to about 0.05 wt. %.

46. The process of item 42, wherein the concentration of the oxidation reaction inhibitor in the first fraction is from about 0.001 wt. % to about 0.01 wt. %.

47. The process of item 42, wherein the concentration of the oxidation reaction inhibitor in the first fraction is from about 0.005 wt. % to about 0.5 wt. %.

48. The process of any item 42, wherein the concentration of the oxidation reaction inhibitor in the first fraction is from about 0.005 wt. % to about 0.1 wt. %.

49. The process of item 42, wherein the concentration of the oxidation reaction inhibitor in the first fraction is from about 0.005 wt. % to about 0.05 wt. %.

50. The process of item 42, wherein the concentration of the oxidation reaction inhibitor in the first fraction is from about 0.005 wt. % to about 0.01 wt. %.

51. The process of item 42, wherein the concentration of the oxidation reaction inhibitor in the first fraction is from about 0.01 wt. % to about 0.5 wt. %.

52. The process of item 42, wherein the concentration of the oxidation reaction inhibitor in the first fraction is from about 0.01 wt. % to about 0.1 wt. %.

53. The process of item 42, wherein the concentration of the oxidation reaction inhibitor in the first fraction is from about 0.01 wt. % to about 0.05 wt. %.

54. The process of item 42, wherein the concentration of the oxidation reaction inhibitor in the first fraction is from about 0.05 wt. % to about 0.5 wt. %.

55. The process of item 42, wherein the concentration of the oxidation reaction inhibitor in the first fraction is from about 0.05 wt. % to about 0.1 wt. %.

56. The process of item 42, wherein the concentration of the oxidation reaction inhibitor in the first fraction is from about 0.1 wt. % to about 0.5 wt. %.

57. A process for preparing a $C_5$-$C_6$ aldaric acid and/or lactone(s) thereof, the process comprising:

feeding a feed mixture comprising at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof to a reaction zone;

reacting the oxidation reactant in the presence of oxygen and an oxidation catalyst in the reaction zone to form a reaction mixture comprising (a) the $C_5$-$C_6$ aldaric acid and/or lactone(s) thereof, (b) unreacted oxidation reactant(s) and/or on-path intermediate(s) thereof, and (c) an oxidation reaction inhibitor;

feeding the reaction mixture to a separation zone to separate at least a portion of the $C_5$-$C_6$ aldaric acid and/or lactone(s) thereof from the reaction mixture and form a product fraction comprising the $C_5$-$C_6$ aldaric acid and/or lactone(s) thereof and a recycle fraction comprising the unreacted oxidation reactant(s) and/or on-path intermediate(s) thereof and the oxidation reaction inhibitor;

removing a first portion of the recycle fraction from the process; and recycling a second portion of the recycle fraction to the reaction zone or feed thereto.

58. The process of item 57, wherein the concentration of the oxidation reaction inhibitor in the second portion of the recycle fraction is about 0.5 wt. % or less, about 0.3 wt. % or less, about 0.1 wt. % or less, about 0.05 wt. % or less, or about 0.01 wt. % or less.

59. The process of item 58, wherein the concentration of the oxidation reaction inhibitor in the second portion of the recycle fraction is about 0.5 wt. % or less.

60. The process of item 58, wherein the concentration of the oxidation reaction inhibitor in the second portion of the recycle fraction is about 0.3 wt. % or less.

61. The process of item 58, wherein the concentration of the oxidation reaction inhibitor in the second portion of the recycle fraction is about 0.1 wt. % or less.

62. The process of item 58, wherein the concentration of the oxidation reaction inhibitor in the second portion of the recycle fraction is about 0.05 wt. % or less.

63. The process of item 58, wherein the concentration of the oxidation reaction inhibitor in the second portion of the recycle fraction is about 0.01 wt. % or less.

64. The process of item 57 or 58, wherein the concentration of the oxidation reaction inhibitor in the second portion of the recycle fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

65. The process of item 64, wherein the concentration of the oxidation reaction inhibitor in the second portion of the recycle fraction is from about 0.001 wt. % to about 0.5 wt. %.

66. The process of item 64, wherein the concentration of the oxidation reaction inhibitor in the second portion of the recycle fraction is from about 0.001 wt. % to about 0.1 wt. %.

67. The process of item 64, wherein the concentration of the oxidation reaction inhibitor in the second portion of the recycle fraction is from about 0.001 wt. % to about 0.05 wt. %.

68. The process of item 64, wherein the concentration of the oxidation reaction inhibitor in the second portion of the recycle fraction is from about 0.001 wt. % to about 0.01 wt. %.

69. The process of item 64, wherein the concentration of the oxidation reaction inhibitor in the second portion of the recycle fraction is from about 0.005 wt. % to about 0.5 wt. %.

70. The process of item 64, wherein the concentration of the oxidation reaction inhibitor in the second portion of the recycle fraction is from about 0.005 wt. % to about 0.1 wt. %.

71. The process of item 64, wherein the concentration of the oxidation reaction inhibitor in the second portion of the recycle fraction is from about 0.005 wt. % to about 0.05 wt. %.

72. The process of item 64, wherein the concentration of the oxidation reaction inhibitor in the second portion of the recycle fraction is from about 0.005 wt. % to about 0.01 wt. %.

73. The process of item 64, wherein the concentration of the oxidation reaction inhibitor in the second portion of the recycle fraction is from about 0.01 wt. % to about 0.5 wt. %.

74. The process of item 64, wherein the concentration of the oxidation reaction inhibitor in the second portion of the recycle fraction is from about 0.01 wt. % to about 0.1 wt. %.

75. The process of item 64, wherein the concentration of the oxidation reaction inhibitor in the second portion of the recycle fraction is from about 0.01 wt. % to about 0.05 wt. %.

76. The process of item 64, wherein the concentration of the oxidation reaction inhibitor in the second portion of the recycle fraction is from about 0.05 wt. % to about 0.5 wt. %.

77. The process of item 64, wherein the concentration of the oxidation reaction inhibitor in the second portion of the recycle fraction is from about 0.05 wt. % to about 0.1 wt. %.

78. The process of item 64, wherein the concentration of the oxidation reaction inhibitor in the second portion of the recycle fraction is from about 0.1 wt. % to about 0.5 wt. %.

79. The process of any one of items 57 to 78, wherein the concentration of the oxidation reactant in the feed mixture is about 1 wt. % or greater, about 5 wt. % or greater, about 10 wt. % or greater, about 15 wt. % or greater, or about 20 wt. % or greater.

80. The process of any one of items 57 to 79, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

81. The process of any one of items 57 to 80, wherein the concentration of the oxidation reactant in the feed mixture is from about 1 wt. % to 50 wt. %.

82. The process of any one of items 57 to 81, wherein the concentration of the oxidation reactant in the feed mixture is from about 1 wt. % to 25 wt. %.

83. The process of any one of items 57 to 82, wherein the concentration of the oxidation reactant in the feed mixture is from about 5 wt. % to 25 wt. %.

84. The process of any one of items 27 to 83, wherein the separation zone comprises a chromatographic separation stage.

85. The process of item 84, wherein the chromatographic separation stage comprises a separation media.

86. The process of item 85, wherein the separation media comprises an amphoteric and/or anionic chromatography resin.

87. The process of any one of the preceding items, wherein the yield of the $C_5$-$C_6$ aldaric acid and/or lactone(s) thereof is about 50% or greater, about 55% or greater, about 60% or greater, about 65% or greater, about 70% or greater, or about 75% or greater.

88. The process of any one of the preceding items, wherein the yield of the $C_5$-$C_6$ aldaric acid and/or lactone(s) thereof is from about 50% to about 85%, from about 50% to about 80%, from about 50% to about 75%, from about 50% to about 70%, from about 50% to about 65%, from about 60% to about 85%, from about 60% to about 80%, from about 60% to about 75%, from about 60% to about 70%, from about 65% to about 85%, from about 65% to about 80%, from about 65% to about 75%, or from about 65% to about 70%.

89. The process of any one of the preceding items, wherein the oxidation reactant comprises the $C_5$-$C_6$ aldose.

90. The process of any one of the preceding items, wherein the $C_5$-$C_6$ aldose is selected from the group consisting of arabinose, lyxose, ribose, xylose, allose, altrose, galactose, glucose, gulose, idose, mannose, talose, and mixtures thereof.

91. The process of any one of the preceding items, wherein the $C_5$-$C_6$ aldose comprises glucose.

92. The process of any one of the preceding items, wherein the $C_5$-$C_6$ aldose is obtained from a carbohydrate-containing source.

93. The process of any one of the preceding items, wherein the $C_5$-$C_6$ aldose is obtained from a grain crop.

94. The process of any one of the preceding items, wherein the oxidation reactant comprises the $C_5$-$C_6$ aldonic acid and/or lactone(s) thereof.

95. The process of any one of the preceding items, wherein the $C_5$-$C_6$ aldonic acid is selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof.

96. The process of any one of the preceding items, wherein the $C_5$-$C_6$ aldonic acid comprises gluconic acid.

97. The process of any one of the preceding items, wherein the oxidation reactant comprises the $C_5$-$C_6$ uronic acid and/or lactone(s) thereof.

98. The process of any one of the preceding items, wherein the $C_5$-$C_6$ uronic acid is selected from the group consisting of arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof.

99. The process of any one of the preceding items, wherein the $C_5$-$C_6$ uronic acid comprises guluronic acid.

100. The process of any one of the preceding items, wherein the reaction mixture comprises a $C_5$-$C_6$ aldaric acid that is selected from the group consisting of arabinaric acid, lyxaric acid, ribaric acid, xylaric acid, allaric acid, altraric acid, galactaric acid, glucaric acid, gularic acid, idaric acid, mannaric acid, talaric acid, and mixtures thereof.

101. The process of any one of the preceding items, wherein the reaction mixture comprises glucaric acid.

102. A process for preparing a $C_5$-$C_6$ uronic acid and/or lactone(s) thereof, the process comprising:

feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a reaction zone; and reacting the oxidation reactant in the presence of oxygen and an oxidation catalyst in the reaction zone to form a reaction mixture comprising the $C_5$-$C_6$ uronic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

103. The process of item 102, wherein the concentration of the oxidation reaction inhibitor in the feed mixture is about 0.5 wt. % or less.

104. The process of item 102, wherein the concentration of the oxidation reaction inhibitor in the feed mixture is about 0.3 wt. % or less.

105. The process of item 102, wherein the concentration of the oxidation reaction inhibitor in the feed mixture is about 0.1 wt. % or less.

106. The process of item 102, wherein the concentration of the oxidation reaction inhibitor in the feed mixture is about 0.05 wt. % or less.

107. The process of item 102, wherein the concentration of the oxidation reaction inhibitor in the feed mixture is about 0.01 wt. % or less.

108. The process of item 102, wherein the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

109. The process of item 108, wherein the concentration of the oxidation reaction inhibitor in the feed mixture is from about 0.001 wt. % to about 0.5 wt. %.

110. The process of item 108, wherein the concentration of the oxidation reaction inhibitor in the feed mixture is from about 0.001 wt. % to about 0.1 wt. %.

111. The process of item 108, wherein the concentration of the oxidation reaction inhibitor in the feed mixture is from about 0.001 wt. % to about 0.05 wt. %.

112. The process of item 108, wherein the concentration of the oxidation reaction inhibitor in the feed mixture is from about 0.001 wt. % to about 0.01 wt. %.

113. The process of item 108, wherein the concentration of the oxidation reaction inhibitor in the feed mixture is from about 0.005 wt. % to about 0.5 wt. %.

114. The process of item 108, wherein the concentration of the oxidation reaction inhibitor in the feed mixture is from about 0.005 wt. % to about 0.1 wt. %.

115. The process of item 108, wherein the concentration of the oxidation reaction inhibitor in the feed mixture is from about 0.005 wt. % to about 0.05 wt. %.

116. The process of item 108, wherein the concentration of the oxidation reaction inhibitor in the feed mixture is from about 0.005 wt. % to about 0.01 wt. %.

117. The process of item 108, wherein the concentration of the oxidation reaction inhibitor in the feed mixture is from about 0.01 wt. % to about 0.5 wt. %.

118. The process of item 108, wherein the concentration of the oxidation reaction inhibitor in the feed mixture is from about 0.01 wt. % to about 0.1 wt. %.

119. The process of item 108, wherein the concentration of the oxidation reaction inhibitor in the feed mixture is from about 0.01 wt. % to about 0.05 wt. %.

120. The process of item 108, wherein the concentration of the oxidation reaction inhibitor in the feed mixture is from about 0.05 wt. % to about 0.5 wt. %.

121. The process of item 108, wherein the concentration of the oxidation reaction inhibitor in the feed mixture is from about 0.05 wt. % to about 0.1 wt. %.

122. The process of item 108, wherein the concentration of the oxidation reaction inhibitor in the feed mixture is from about 0.1 wt. % to about 0.5 wt. %.

123. The process of items 102 to 122, wherein the concentration of the oxidation reactant in the feed mixture is about 1 wt. % or greater, about 5 wt. % or greater, about 10 wt. % or greater, about 15 wt. % or greater, or about 20 wt. % or greater.

124. The process of any one of items 102 to 123, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

125. The process of any one of items 102 to 124, wherein the concentration of the oxidation reactant in the feed mixture is from about 1 wt. % to 50 wt. %.

126. The process of any one of items 102 to 125, wherein the concentration of the oxidation reactant in the feed mixture is from about 1 wt. % to 25 wt. %.

127. The process of any one of items 102 to 126, wherein the concentration of the oxidation reactant in the feed mixture is from about 5 wt. % to 25 wt. %.

128. A process for preparing a $C_5$-$C_6$ uronic acid and/or lactone(s) thereof, the process comprising:

feeding a feed mixture comprising (a) at least one oxidation reactant selected from the group consisting of a $C_5$-$C_6$ aldose, a $C_5$-$C_6$ aldonic acid and/or lactone(s) thereof, and mixtures thereof and (b) an oxidation reaction inhibitor to a separation zone to separate at least a portion of the oxidation reaction inhibitor from the mixture and form a first fraction comprising at least a portion of the oxidation reactant and a second fraction comprising at least a portion of the oxidation reaction inhibitor;

feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ uronic acid and/or lactone(s) thereof.

129. The process of item 128, wherein the molar ratio of the oxidation reaction inhibitor to the oxidation reactant in the first fraction is less than the molar ratio of the oxidation reaction inhibitor to oxidation reactant in the feed mixture.

130. The process of item 128 or 129, wherein the molar ratio of the oxidation reaction inhibitor to oxidation reactant in the first fraction is less than the molar ratio of the oxidation reaction inhibitor to oxidation reactant in the second fraction.

131. The process of any one of items 128 to 130, wherein the concentration of the oxidation reactant in the first fraction is about 1 wt. % or greater, about 5 wt. % or greater, about 10 wt. % or greater, about 15 wt. % or greater, or about 20 wt. % or greater.

132. The process of any one of items 128 to 131, wherein the concentration of the oxidation reactant in the first fraction is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

133. The process of any one of items 128 to 132, wherein the concentration of the oxidation reactant in the first fraction is from about 1 wt. % to 50 wt. %.

134. The process of any one of items 128 to 133, wherein the concentration of the oxidation reactant in the first fraction is from about 1 wt. % to 25 wt. %.

135. The process of any one of items 128 to 134, wherein the concentration of the oxidation reactant in the first fraction is from about 5 wt. % to 25 wt. %.

136. The process of any one of items 128 to 135, wherein the concentration of the oxidation reaction inhibitor in the first fraction is less than the concentration of the oxidation reaction inhibitor in the second fraction.

137. The process of any one of items 128 to 136, wherein the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less.

138. The process of item 137, wherein the concentration of the oxidation reaction inhibitor in the first fraction is about 0.5 wt. % or less.

139. The process of item 137, wherein the concentration of the oxidation reaction inhibitor in the first fraction is about 0.3 wt. % or less.

140. The process of item 137, wherein the concentration of the oxidation reaction inhibitor in the first fraction is about 0.1 wt. % or less.

141. The process of item 137, wherein the concentration of the oxidation reaction inhibitor in the first fraction is about 0.05 wt. % or less.

142. The process of item 137, wherein the concentration of the oxidation reaction inhibitor in the first fraction is about 0.01 wt. % or less.

143. The process of any one of items 128 to 137, wherein the concentration of the oxidation reaction inhibitor in the first fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

144. The process of item 143, wherein the concentration of the oxidation reaction inhibitor in the first fraction is from about 0.001 wt. % to about 0.5 wt. %.

145. The process of item 143, wherein the concentration of the oxidation reaction inhibitor in the first fraction is from about 0.001 wt. % to about 0.1 wt. %.

146. The process of item 143, wherein the concentration of the oxidation reaction inhibitor in the first fraction is from about 0.001 wt. % to about 0.05 wt. %.

147. The process of item 143, wherein the concentration of the oxidation reaction inhibitor in the first fraction is from about 0.001 wt. % to about 0.01 wt. %.

148. The process of item 143, wherein the concentration of the oxidation reaction inhibitor in the first fraction is from about 0.005 wt. % to about 0.5 wt. %.

149. The process of item 143, wherein the concentration of the oxidation reaction inhibitor in the first fraction is from about 0.005 wt. % to about 0.1 wt. %.

150. The process of item 143, wherein the concentration of the oxidation reaction inhibitor in the first fraction is from about 0.005 wt. % to about 0.05 wt. %.

151. The process of item 143, wherein the concentration of the oxidation reaction inhibitor in the first fraction is from about 0.005 wt. % to about 0.01 wt. %.

152. The process of item 143, wherein the concentration of the oxidation reaction inhibitor in the first fraction is from about 0.01 wt. % to about 0.5 wt. %.

153. The process of item 143, wherein the concentration of the oxidation reaction inhibitor in the first fraction is from about 0.01 wt. % to about 0.1 wt. %.

154. The process of item 143, wherein the concentration of the oxidation reaction inhibitor in the first fraction is from about 0.01 wt. % to about 0.05 wt. %.

155. The process of item 143, wherein the concentration of the oxidation reaction inhibitor in the first fraction is from about 0.05 wt. % to about 0.5 wt. %.

156. The process of item 143, wherein the concentration of the oxidation reaction inhibitor in the first fraction is from about 0.05 wt. % to about 0.1 wt. %.

157. The process of item 143, wherein the concentration of the oxidation reaction inhibitor in the first fraction is from about 0.1 wt. % to about 0.5 wt. %.

158. A process for preparing a $C_5$-$C_6$ uronic acid and/or lactone(s) thereof, the process comprising:

feeding a feed mixture comprising at least one oxidation reactant selected from the group consisting of a $C_5$-$C_6$ aldose, a $C_5$-$C_6$ aldonic acid and/or lactone(s) thereof, and mixtures thereof to a reaction zone;

reacting the oxidation reactant in the presence of oxygen and an oxidation catalyst in the reaction zone to form a reaction mixture comprising (a) the $C_5$-$C_6$ uronic acid and/or lactone(s) thereof, (b) unreacted oxidation reactant(s) and/or on-path intermediate(s) thereof, and (c) an oxidation reaction inhibitor;

feeding the reaction mixture to a separation zone to separate at least a portion of the $C_5$-$C_6$ uronic acid and/or lactone(s) thereof from the reaction mixture and form a product fraction comprising the $C_5$-$C_6$ uronic acid and/or lactone(s) thereof and a recycle fraction comprising the unreacted oxidation reactant(s) and/or on-path intermediate(s) thereof and the oxidation reaction inhibitor;

removing a first portion of the recycle fraction from the process; and recycling a second portion of the recycle fraction to the reaction zone or feed thereto.

159. The process of item 158, wherein the concentration of the oxidation reaction inhibitor in the second portion of the recycle fraction is about 0.5 wt. % or less, about 0.3 wt. % or less, about 0.1 wt. % or less, about 0.05 wt. % or less, or about 0.01 wt. % or less.

160. The process of item 159, wherein the concentration of the oxidation reaction inhibitor in the second portion of the recycle fraction is about 0.5 wt. % or less.

161. The process of item 159, wherein the concentration of the oxidation reaction inhibitor in the second portion of the recycle fraction is about 0.3 wt. % or less.

162. The process of item 159, wherein the concentration of the oxidation reaction inhibitor in the second portion of the recycle fraction is about 0.1 wt. % or less.

163. The process of item 159, wherein the concentration of the oxidation reaction inhibitor in the second portion of the recycle fraction is about 0.05 wt. % or less.

164. The process of item 159, wherein the concentration of the oxidation reaction inhibitor in the second portion of the recycle fraction is about 0.01 wt. % or less.

165. The process of item 158 or 159, wherein the concentration of the oxidation reaction inhibitor in the second portion of the recycle fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

166. The process of item 165, wherein the concentration of the oxidation reaction inhibitor in the second portion of the recycle fraction is from about 0.001 wt. % to about 0.5 wt. %.

167. The process of item 165, wherein the concentration of the oxidation reaction inhibitor in the second portion of the recycle fraction is from about 0.001 wt. % to about 0.1 wt. %.

168. The process of item 165, wherein the concentration of the oxidation reaction inhibitor in the second portion of the recycle fraction is from about 0.001 wt. % to about 0.05 wt. %.
169. The process of item 165, wherein the concentration of the oxidation reaction inhibitor in the second portion of the recycle fraction is from about 0.001 wt. % to about 0.01 wt. %.
170. The process of item 165, wherein the concentration of the oxidation reaction inhibitor in the second portion of the recycle fraction is from about 0.005 wt. % to about 0.5 wt. %.
171. The process of item 165, wherein the concentration of the oxidation reaction inhibitor in the second portion of the recycle fraction is from about 0.005 wt. % to about 0.1 wt. %.
172. The process of item 165, wherein the concentration of the oxidation reaction inhibitor in the second portion of the recycle fraction is from about 0.005 wt. % to about 0.05 wt. %.
173. The process of item 165, wherein the concentration of the oxidation reaction inhibitor in the second portion of the recycle fraction is from about 0.005 wt. % to about 0.01 wt. %. 174. The process of item 165, wherein the concentration of the oxidation reaction inhibitor in the second portion of the recycle fraction is from about 0.01 wt. % to about 0.5 wt. %.
175. The process of item 165, wherein the concentration of the oxidation reaction inhibitor in the second portion of the recycle fraction is from about 0.01 wt. % to about 0.1 wt. %.
176. The process of item 165, wherein the concentration of the oxidation reaction inhibitor in the second portion of the recycle fraction is from about 0.01 wt. % to about 0.05 wt. %.
177. The process of item 165, wherein the concentration of the oxidation reaction inhibitor in the second portion of the recycle fraction is from about 0.05 wt. % to about 0.5 wt. %.
178. The process of item 165, wherein the concentration of the oxidation reaction inhibitor in the second portion of the recycle fraction is from about 0.05 wt. % to about 0.1 wt. %.
179. The process of item 165, wherein the concentration of the oxidation reaction inhibitor in the second portion of the recycle fraction is from about 0.1 wt. % to about 0.5 wt. %.
180. The process of any one of items 158 to 179, wherein the concentration of the oxidation reactant in the feed mixture is about 1 wt. % or greater, about 5 wt. % or greater, about 10 wt. % or greater, about 15 wt. % or greater, or about 20 wt. % or greater.
181. The process of any one of items 158 to 180, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.
182. The process of any one of items 158 to 181, wherein the concentration of the oxidation reactant in the feed mixture is from about 1 wt. % to 50 wt. %.
183. The process of any one of items 158 to 182, wherein the concentration of the oxidation reactant in the feed mixture is from about 1 wt. % to 25 wt. %.
184. The process of any one of items 158 to 183, wherein the concentration of the oxidation reactant in the feed mixture is from about 5 wt. % to 25 wt. %.
185. The process of any one of items 158 to 184, wherein the separation zone comprises a chromatographic separation stage.
186. The process of item 185, wherein the chromatographic separation stage comprises a separation media.
187. The process of item 186, wherein the separation media comprises an amphoteric and/or anionic chromatography resin.
188. The process of any one of items 102 to 187, wherein the yield of the $C_5$-$C_6$ uronic acid and/or lactone(s) thereof is about 50% or greater, about 55% or greater, about 60% or greater, about 65% or greater, about 70% or greater, or about 75% or greater.
189. The process of any one of items 102 to 188, wherein the yield of the $C_5$-$C_6$ uronic acid and/or lactone(s) thereof is from about 50% to about 85%, from about 50% to about 80%, from about 50% to about 75%, from about 50% to about 70%, from about 50% to about 65%, from about 60% to about 85%, from about 60% to about 80%, from about 60% to about 75%, from about 60% to about 70%, from about 65% to about 85%, from about 65% to about 80%, from about 65% to about 75%, or from about 65% to about 70%.
190. The process of any one of items 102 to 189, wherein the oxidation reactant comprises the $C_5$-$C_6$ aldose.
191. The process of any one of items 102 to 190, wherein the $C_5$-$C_6$ aldose is selected from the group consisting of arabinose, lyxose, ribose, xylose, allose, altrose, galactose, glucose, gulose, idose, mannose, talose, and mixtures thereof. 192. The process of any one of items 102 to 191, wherein the $C_5$-$C_6$ aldose comprises glucose.
193. The process of any one of items 102 to 192, wherein the $C_5$-$C_6$ aldose is obtained from a carbohydrate-containing source.
194. The process of any one of items 102 to 193, wherein the $C_5$-$C_6$ aldose is obtained from a grain crop.
195. The process of any one of items 102 to 194, wherein the oxidation reactant comprises the $C_5$-$C_6$ aldonic acid and/or lactone(s) thereof.
196. The process of any one of items 102 to 195, wherein the $C_5$-$C_6$ aldonic acid is selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof.
197. The process of any one of items 102 to 196, wherein the $C_5$-$C_6$ aldonic acid comprises gluconic acid.
198. The process of any one of items 102 to 197, wherein the reaction mixture comprises a $C_5$-$C_6$ uronic acid that is selected from the group consisting of arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof.
199. The process of any one of items 102 to 198, wherein the reaction mixture comprises guluronic acid.
200. A process for preparing a $C_5$-$C_6$ aldonic acid and/or lactone(s) thereof, the process comprising:
    feeding a feed mixture comprising (a) an oxidation reactant comprising a $C_5$-$C_6$ aldose and (b) an oxidation reaction inhibitor to a reaction zone; and
    reacting the oxidation reactant in the presence of oxygen and an oxidation catalyst in the reaction zone to form a reaction mixture comprising the $C_5$-$C_6$ aldonic acid and/or lactone(s) thereof, wherein the concentration of the oxidation reaction inhibitor in the feed mixture is about 0.5 wt. % or less, about 0.3 wt. % or less, about 0.1 wt. % or less, about 0.05 wt. % or less, or about 0.01 wt. % or less.

201. The process of item 200, wherein the concentration of the oxidation reaction inhibitor in the feed mixture is about 0.5 wt. % or less.

202. The process of item 200, wherein the concentration of the oxidation reaction inhibitor in the feed mixture is about 0.3 wt. % or less.

203. The process of item 200, wherein the concentration of the oxidation reaction inhibitor in the feed mixture is about 0.1 wt. % or less.

204. The process of item 200, wherein the concentration of the oxidation reaction inhibitor in the feed mixture is about 0.05 wt. % or less.

205. The process of item 200, wherein the concentration of the oxidation reaction inhibitor in the feed mixture is about 0.01 wt. % or less.

206. The process of item 200, wherein the concentration of the oxidation reaction inhibitor in the feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

207. The process of item 206, wherein the concentration of the oxidation reaction inhibitor in the feed mixture is from about 0.001 wt. % to about 0.5 wt. %.

208. The process of item 206, wherein the concentration of the oxidation reaction inhibitor in the feed mixture is from about 0.001 wt. % to about 0.1 wt. %.

209. The process of item 206, wherein the concentration of the oxidation reaction inhibitor in the feed mixture is from about 0.001 wt. % to about 0.05 wt. %.

210. The process of item 206, wherein the concentration of the oxidation reaction inhibitor in the feed mixture is from about 0.001 wt. % to about 0.01 wt. %.

211. The process of item 206, wherein the concentration of the oxidation reaction inhibitor in the feed mixture is from about 0.005 wt. % to about 0.5 wt. %.

212. The process of item 206, wherein the concentration of the oxidation reaction inhibitor in the feed mixture is from about 0.005 wt. % to about 0.1 wt. %.

213. The process of item 206, wherein the concentration of the oxidation reaction inhibitor in the feed mixture is from about 0.005 wt. % to about 0.05 wt. %.

214. The process of item 206, wherein the concentration of the oxidation reaction inhibitor in the feed mixture is from about 0.005 wt. % to about 0.01 wt. %.

215. The process of item 206, wherein the concentration of the oxidation reaction inhibitor in the feed mixture is from about 0.01 wt. % to about 0.5 wt. %.

216. The process of item 206, wherein the concentration of the oxidation reaction inhibitor in the feed mixture is from about 0.01 wt. % to about 0.1 wt. %.

217. The process of item 206, wherein the concentration of the oxidation reaction inhibitor in the feed mixture is from about 0.01 wt. % to about 0.05 wt. %.

218. The process of item 206, wherein the concentration of the oxidation reaction inhibitor in the feed mixture is from about 0.05 wt. % to about 0.5 wt. %.

219. The process of item 206, wherein the concentration of the oxidation reaction inhibitor in the feed mixture is from about 0.05 wt. % to about 0.1 wt. %.

220. The process of item 206, wherein the concentration of the oxidation reaction inhibitor in the feed mixture is from about 0.1 wt. % to about 0.5 wt. %.

221. The process of items 200 to 220, wherein the concentration of the oxidation reactant in the feed mixture is about 1 wt. % or greater, about 5 wt. % or greater, about 10 wt. % or greater, about 15 wt. % or greater, or about 20 wt. % or greater.

222. The process of any one of items 200 to 221, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

223. The process of item 222, wherein the concentration of the oxidation reactant in the feed mixture is from about 1 wt. % to 50 wt. %.

224. The process of item 222, wherein the concentration of the oxidation reactant in the feed mixture is from about 1 wt. % to 25 wt. %.

225. The process of item 222, wherein the concentration of the oxidation reactant in the feed mixture is from about 5 wt. % to 25 wt. %.

226. A process for preparing a $C_5$-$C_6$ aldonic acid and/or lactone(s) thereof, the process comprising:

feeding a feed mixture comprising (a) an oxidation reactant comprising a $C_5$-$C_6$ aldose and (b) an oxidation reaction inhibitor to a separation zone to separate at least a portion of the oxidation reaction inhibitor from the mixture and form a first fraction comprising at least a portion of the oxidation reactant and a second fraction comprising at least a portion of the oxidation reaction inhibitor;

feeding at least a portion of the first fraction comprising the oxidation reactant to a reaction zone; and reacting the oxidation reactant in the presence of oxygen and an oxidation catalyst in the reaction zone to form a reaction mixture comprising the $C_5$-$C_6$ aldonic acid and/or lactone(s) thereof.

227. The process of item 226, wherein the molar ratio of the oxidation reaction inhibitor to the oxidation reactant in the first fraction is less than the molar ratio of the oxidation reaction inhibitor to oxidation reactant in the feed mixture.

228. The process of item 226 or 227, wherein the molar ratio of the oxidation reaction inhibitor to oxidation reactant in the first fraction is less than the molar ratio of the oxidation reaction inhibitor to oxidation reactant in the second fraction.

229. The process of any one of items 226 to 228, wherein the concentration of the oxidation reactant in the first fraction is about 1 wt. % or greater, about 5 wt. % or greater, about 10 wt. % or greater, about 15 wt. % or greater, or about 20 wt. % or greater.

230. The process of any one of items 226 to 229, wherein the concentration of the oxidation reactant in the first fraction is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

231. The process of any one of items 226 to 230, wherein the concentration of the oxidation reactant in the first fraction is from about 1 wt. % to 50 wt. %.

232. The process of any one of items 226 to 231, wherein the concentration of the oxidation reactant in the first fraction is from about 1 wt. % to 25 wt. %.

233. The process of any one of items 226 to 232, wherein the concentration of the oxidation reactant in the first fraction is from about 5 wt. % to 25 wt. %.

234. The process of any one of items 226 to 233, wherein the concentration of the oxidation reaction inhibitor in the first fraction is less than the concentration of the oxidation reaction inhibitor in the second fraction.

235. The process of any one of items 226 to 234, wherein the concentration of the oxidation reaction inhibitor in the first fraction is about 0.5 wt. % or less, about 0.3 wt. % or less, about 0.1 wt. % or less, about 0.05 wt. % or less, or about 0.01 wt. % or less.

236. The process of item 235, wherein the concentration of the oxidation reaction inhibitor in the first fraction is about 0.5 wt. % or less.

237. The process of item 235, wherein the concentration of the oxidation reaction inhibitor in the first fraction is about 0.3 wt. % or less.

238. The process of item 235, wherein the concentration of the oxidation reaction inhibitor in the first fraction is about 0.1 wt. % or less.

239. The process of item 235, wherein the concentration of the oxidation reaction inhibitor in the first fraction is about 0.05 wt. % or less.

240. The process of item 235, wherein the concentration of the oxidation reaction inhibitor in the first fraction is about 0.01 wt. % or less.

241. The process of any one of items 226 to 235, wherein the concentration of the oxidation reaction inhibitor in the first fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

242. The process of item 241, wherein the concentration of the oxidation reaction inhibitor in the first fraction is from about 0.001 wt. % to about 0.5 wt. %.

243. The process of item 241, wherein the concentration of the oxidation reaction inhibitor in the first fraction is from about 0.001 wt. % to about 0.1 wt. %.

244. The process of item 241, wherein the concentration of the oxidation reaction inhibitor in the first fraction is from about 0.001 wt. % to about 0.05 wt. %.

245. The process of item 241, wherein the concentration of the oxidation reaction inhibitor in the first fraction is from about 0.001 wt. % to about 0.01 wt. %.

246. The process of item 241, wherein the concentration of the oxidation reaction inhibitor in the first fraction is from about 0.005 wt. % to about 0.5 wt. %.

247. The process of item 241, wherein the concentration of the oxidation reaction inhibitor in the first fraction is from about 0.005 wt. % to about 0.1 wt. %.

248. The process of item 241, wherein the concentration of the oxidation reaction inhibitor in the first fraction is from about 0.005 wt. % to about 0.05 wt. %.

249. The process of item 241, wherein the concentration of the oxidation reaction inhibitor in the first fraction is from about 0.005 wt. % to about 0.01 wt. %.

250. The process of item 241, wherein the concentration of the oxidation reaction inhibitor in the first fraction is from about 0.01 wt. % to about 0.5 wt. %.

251. The process of item 241, wherein the concentration of the oxidation reaction inhibitor in the first fraction is from about 0.01 wt. % to about 0.1 wt. %.

252. The process of item 241, wherein the concentration of the oxidation reaction inhibitor in the first fraction is from about 0.01 wt. % to about 0.05 wt. %.

253. The process of item 241, wherein the concentration of the oxidation reaction inhibitor in the first fraction is from about 0.05 wt. % to about 0.5 wt. %.

254. The process of item 241, wherein the concentration of the oxidation reaction inhibitor in the first fraction is from about 0.05 wt. % to about 0.1 wt. %.

255. The process of item 241, wherein the concentration of the oxidation reaction inhibitor in the first fraction is from about 0.1 wt. % to about 0.5 wt. %.

256. A process for preparing a $C_5$-$C_6$ aldonic acid and/or lactone(s) thereof, the process comprising:
  feeding a feed mixture comprising an oxidation reactant comprising a $C_5$-$C_6$ aldose to a reaction zone;
  reacting the oxidation reactant in the presence of oxygen and an oxidation catalyst in the reaction zone to form a reaction mixture comprising (a) the $C_5$-$C_6$ aldonic acid and/or lactone(s) thereof, (b) unreacted oxidation reactant(s) and/or on-path intermediate(s) thereof, and (c) an oxidation reaction inhibitor;
  feeding the reaction mixture to a separation zone to separate at least a portion of the $C_5$-$C_6$ aldonic acid and/or lactone(s) thereof from the reaction mixture and form a product fraction comprising the $C_5$-$C_6$ aldonic acid and/or lactone(s) thereof and a recycle fraction comprising the unreacted oxidation reactant(s) and/or on-path intermediate(s) thereof and the oxidation reaction inhibitor;
  removing a first portion of the recycle fraction from the process; and
  recycling a second portion of the recycle fraction to the reaction zone or feed thereto.

257. The process of item 256, wherein the concentration of the oxidation reaction inhibitor in the second portion of the recycle fraction is about 0.5 wt. % or less, about 0.3 wt. % or less, about 0.1 wt. % or less, about 0.05 wt. % or less, or about 0.01 wt. % or less.

258. The process of item 257, wherein the concentration of the oxidation reaction inhibitor in the second portion of the recycle fraction is about 0.5 wt. % or less.

259. The process of item 257, wherein the concentration of the oxidation reaction inhibitor in the second portion of the recycle fraction is about 0.3 wt. % or less.

260. The process of item 257, wherein the concentration of the oxidation reaction inhibitor in the second portion of the recycle fraction is about 0.1 wt. % or less.
261. The process of item 257, wherein the concentration of the oxidation reaction inhibitor in the second portion of the recycle fraction is about 0.05 wt. % or less.
262. The process of item 257, wherein the concentration of the oxidation reaction inhibitor in the second portion of the recycle fraction is about 0.01 wt. % or less.
263. The process of item 256 or 257, wherein the concentration of the oxidation reaction inhibitor in the second portion of the recycle fraction is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.
264. The process of item 263, wherein the concentration of the oxidation reaction inhibitor in the second portion of the recycle fraction is from about 0.001 wt. % to about 0.5 wt. %.
265. The process of item 263, wherein the concentration of the oxidation reaction inhibitor in the second portion of the recycle fraction is from about 0.001 wt. % to about 0.1 wt. %.
266. The process of item 263, wherein the concentration of the oxidation reaction inhibitor in the second portion of the recycle fraction is from about 0.001 wt. % to about 0.05 wt. %.
267. The process of item 263, wherein the concentration of the oxidation reaction inhibitor in the second portion of the recycle fraction is from about 0.001 wt. % to about 0.01 wt. %.
268. The process of item 263, wherein the concentration of the oxidation reaction inhibitor in the second portion of the recycle fraction is from about 0.005 wt. % to about 0.5 wt. %.
269. The process of item 263, wherein the concentration of the oxidation reaction inhibitor in the second portion of the recycle fraction is from about 0.005 wt. % to about 0.1 wt. %.
270. The process of item 263, wherein the concentration of the oxidation reaction inhibitor in the second portion of the recycle fraction is from about 0.005 wt. % to about 0.05 wt. %.
271. The process of item 263, wherein the concentration of the oxidation reaction inhibitor in the second portion of the recycle fraction is from about 0.005 wt. % to about 0.01 wt. %.
272. The process of item 263, wherein the concentration of the oxidation reaction inhibitor in the second portion of the recycle fraction is from about 0.01 wt. % to about 0.5 wt. %.
273. The process of item 263, wherein the concentration of the oxidation reaction inhibitor in the second portion of the recycle fraction is from about 0.01 wt. % to about 0.1 wt. %.
274. The process of item 263, wherein the concentration of the oxidation reaction inhibitor in the second portion of the recycle fraction is from about 0.01 wt. % to about 0.05 wt. %.
275. The process of item 263, wherein the concentration of the oxidation reaction inhibitor in the second portion of the recycle fraction is from about 0.05 wt. % to about 0.5 wt. %.
276. The process of item 263, wherein the concentration of the oxidation reaction inhibitor in the second portion of the recycle fraction is from about 0.05 wt. % to about 0.1 wt. %.
277. The process of item 263, wherein the concentration of the oxidation reaction inhibitor in the second portion of the recycle fraction is from about 0.1 wt. % to about 0.5 wt. %.
278. The process of any one of items 256 to 277, wherein the concentration of the oxidation reactant in the feed mixture is about 1 wt. % or greater, about 5 wt. % or greater, about 10 wt. % or greater, about 15 wt. % or greater, or about 20 wt. % or greater.
279. The process of any one of items 256 to 278, wherein the concentration of the oxidation reactant in the feed mixture is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.
280. The process of any one of items 256 to 279, wherein the concentration of the oxidation reactant in the feed mixture is from about 1 wt. % to 50 wt. %.
281. The process of any one of items 256 to 280, wherein the concentration of the oxidation reactant in the feed mixture is from about 1 wt. % to about 25 wt. %.
282. The process of any one of items 256 to 281, wherein the concentration of the oxidation reactant in the feed mixture is from about 5 wt. % to 25 wt. %.
283. The process of any one of items 256 to 282, wherein the separation zone comprises a chromatographic separation stage.
284. The process of item 283, wherein the chromatographic separation stage comprises a separation media.
285. The process of item 284, wherein the separation media comprises an amphoteric and/or anionic chromatography resin.
286. The process of any one of items 200 to 285, wherein the yield of the $C_5$-$C_6$ aldonic acid and/or lactone(s) thereof is about 50% or greater, about 55% or greater, about 60% or greater, about 65% or greater, about 70% or greater, or about 75% or greater.
287. The process of any one of items 200 to 286, wherein the yield of the $C_5$-$C_6$ aldonic acid and/or lactone(s) thereof is from about 50% to about 85%, from about 50% to about 80%, from about 50% to about 75%, from about 50% to about 70%, from about 50% to about 65%, from about 60% to about 85%, from about 60% to about 80%, from about 60% to about 75%, from about 60% to about 70%, from about 65% to about 85%, from about 65% to about 80%, from about 65% to about 75%, or from about 65% to about 70%.
288. The process of any one of items 200 to 287, wherein the $C_5$-$C_6$ aldose is selected from the group consisting of arabinose, lyxose, ribose, xylose, allose, altrose, galactose, glucose, gulose, idose, mannose, talose, and mixtures thereof.
289. The process of any one of items 200 to 288, wherein the $C_5$-$C_6$ aldose comprises glucose.
290. The process of any one of items 200 to 289, wherein the $C_5$-$C_6$ aldose is obtained from a carbohydrate-containing source.

291. The process of any one of items 200 to 290, wherein the $C_5$-$C_6$ aldose is obtained from a grain crop.
292. The process of any one of items 200 to 291, wherein the reaction mixture comprises a $C_5$-$C_6$ aldonic acid that is selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof.
293. The process of any one of items 200 to 292, wherein the reaction mixture comprises gluconic acid.
294. The process of any one of the preceding items, wherein the oxidation reaction inhibitor comprises a $C_3$ alcohol and/or a $C_3$ acid.
295. The process of any one of the preceding items, wherein the oxidation reaction inhibitor comprises a $C_3$ alcohol.
296. The process of any one of the preceding items, wherein the oxidation reaction inhibitor comprises a $C_3$ acid.
297. The process of any one of the preceding items, wherein the oxidation reaction inhibitor comprises a $C_3$ alcohol and a $C_3$ acid.
298. The process of any one of the preceding items, wherein the oxidation reaction inhibitor comprises at least one component selected from the group consisting of glyceric acid, 3-hydroxypropionic acid, 1,3-propanediol, and mixtures thereof.
299. The process of any one of the preceding items, wherein the oxidation reaction inhibitor comprises glyceric acid.
300. The process of any one of the preceding items, wherein the oxidation reaction inhibitor comprises 3-hydroxypropionic acid.
301. The process of any one of the preceding items, wherein the oxidation catalyst comprises a catalytically active phase.
302. The process of item 301, wherein the molar ratio of the oxidation reaction inhibitor to the catalytically active phase is about 50:1 or less, about 40:1 or less, about 30:1 or less, about 20:1 or less, about 10:1 or less, about 5:1 or less, about 1:1 or less, or about 0.1:1 or less.
303. The process of item 301 or 302, wherein the molar ratio of the oxidation reaction inhibitor to the catalytically active phase is from about 0.001:1 to about 50:1, from about 0.001:1 to about 20:1, from about 0.001:1 to about 10:1, from about 0.001:1 to about 1:1, from about 0.001:1 to about 0.1:1, from about 0.001:1 to about 0.01:1, from about 0.01:1 to about 50:1, from about 0.01:1 to about 20:1, from about 0.01:1 to about 10:1, from about 0.01:1 to about 1:1, from about 0.01:1 to about 0.1:1, from about 0.1:1 to about 50:1, from about 0.1:1 to about 20:1, from about 0.1:1 to about 10:1, from about 0.1:1 to about 1:1, from about 1:1 to about 50:1, from about 1:1 to about 20:1, or from about 1:1 to about 10:1.
304. The process of any one of items 301 to 303, wherein the catalytically active phase comprises one or more noble metals.
305. The process of any one of items 301 to 304, wherein the catalytically active phase comprises platinum and/or gold.
306. The process of any one of items 301 to 305, wherein the catalytically active phase comprises platinum.
307. The process of any one of items 301 to 305, wherein the catalytically active phase comprises gold.
308. The process of any one of items 301 to 305, wherein the catalytically active phase comprises platinum and gold.
309. The process of any one of items 301 to 308, wherein the oxidation catalyst has a loading of the catalytically active phase of about 10 wt. % or less, about 7.5 wt. % or less, about 5 wt. % or less, about 4 wt. % or less, about 2 wt. % or less, or about 1 wt. % or less.
310. The process of any one of items 301 to 309, wherein the oxidation catalyst has a loading of the catalytically active phase of about 0.1 wt. % or greater, about 0.25 wt. % or greater, about 0.5 wt. % or greater, about 0.75 wt. % or greater, or about 1 wt. % or greater.
311. The process of any one of items 301 to 310, wherein the oxidation catalyst has a loading of the catalytically active phase of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 1 wt. % to about 10 wt. %, from about 1 wt. % to about 7.5 wt. %, from about 1 wt. % to about 5 wt. %, from about 1 wt. % to about 4 wt. %, or from about 1 wt. % to about 3 wt. %.
312. The process of any one of items 301 to 311, wherein the oxidation catalyst has a loading of the catalytically active phase of from about 0.1 wt. % to about 10 wt. %.
313. The process of any one of items 301 to 312, wherein the oxidation catalyst has a loading of the catalytically active phase of from about 0.1 wt. % to about 5 wt. %.
314. The process of any one of items 301 to 313, wherein the oxidation catalyst has a loading of the catalytically active phase of from about 0.5 wt. % to about 5 wt. %.
315. The process of any one of the preceding items, wherein the oxidation catalyst is a heterogeneous catalyst.
316. The process of any one of the preceding items, wherein the oxidation catalyst comprises a catalyst support.
317. The process of item 316, wherein the support of the oxidation catalyst comprises a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof.
318. The process of item 316 or 317, wherein the support of the oxidation catalyst comprises carbon, titania, zirconia, or combinations thereof.
319. The process of any one of items 316 to 318, wherein the support of the oxidation catalyst comprises at least one carbon material selected from the group consisting of graphite, carbon black, activated carbon and combinations thereof.
320. The process of any one of items 316 to 319, wherein the support of the oxidation catalyst comprises zirconia, doped zirconia, doped zirconia-metal composite, doped zirconia-metal oxide composite, titania, doped titania, doped titania-metal composite, doped titania-metal oxide composite, or mixtures thereof.
321. The process of any one of the preceding items, wherein the oxidation catalyst has a BET specific surface area that is at least about 5 $m^2/g$, at least about 100 $m^2/g$, at least about 200 $m^2/g$, at least about 500 $m^2/g$, at least about 1,000 $m^2/g$, at least about 1,500 $m^2/g$, or at least about 2,000 $m^2/g$.
322. The process of any one of the preceding items, wherein the oxidation catalyst has a BET specific surface area that is from about 5 $m^2/g$ to about 2,500 $m^2/g$, from about 5 $m^2/g$ to about 2,000 $m^2/g$, from about 5 $m^2/g$ to about 1,500 $m^2/g$, from about 5 $m^2/g$ to about 1,000 $m^2/g$, from about 5 $m^2/g$ to about 500 $m^2/g$, from about 5 $m^2/g$ to about 200 $m^2/g$, from about 100 $m^2/g$ to about 2,500 $m^2/g$, from about 100 $m^2/g$ to about 2,000 $m^2/g$, from about 100 $m^2/g$ to about 1,500 $m^2/g$, from about 100 $m^2/g$ to about 1,000 $m^2/g$, from about 100 $m^2/g$ to about 500 $m^2/g$, or from about 100 $m^2/g$ to about 200 $m^2/g$.

323. The process of any one of the preceding items, wherein the oxidation catalyst has a BET specific surface area that is from about 100 m²/g to about 200 m²/g.

324. The process of any one of the preceding items, wherein the oxidation catalyst comprises a first catalyst comprising platinum and a second catalyst comprising gold, wherein the first and second catalyst are different.

325. The process of item 324, wherein the reaction zone comprises a mixture of the first catalyst and second catalyst.

326. The process of item 324 or 325, wherein the reaction zone comprises a first stage comprising the first catalyst and a second stage comprising the second catalyst.

327. The process of any one of items 324 to 326, wherein the reaction zone comprises a first stage and the first stage comprises a mixture of the first catalyst and the second catalyst and the weight or volume of the first catalyst is greater than the weight or volume of the second catalyst.

328. The process of any one of items 324 to 327, wherein the reaction zone comprises a first stage and the first stage comprises a mixture of the first catalyst and the second catalyst and the weight or volumetric ratio of the first catalyst to the second catalyst is about 2:1 or greater, about 3:1 or greater, or about 4:1 or greater.

329. The process of any one of items 324 to 328, wherein the reaction zone comprises a first stage and the first stage comprises a mixture of the first catalyst and the second catalyst and the weight or volumetric ratio of the first catalyst to the second catalyst is from about 2:1 to about 10:1, from about 2:1 to about 5:1, from about 3:1 to about 10:1, or from about 3:1 to about 5:1.

330. The process of any one of items 328 to 329, wherein the ratio of the first catalyst to the second catalyst referred to is the volumetric ratio.

331. The process of any one of items 324 to 330, wherein the reaction zone comprises a second stage and the second stage comprises a mixture of the first catalyst and the second catalyst and the weight or volume of the second catalyst is greater than the weight or volume of the first catalyst.

332. The process of any one of items 324 to 331, wherein the reaction zone comprises a second stage and the second stage comprises a mixture of the first catalyst and the second catalyst and the weight or volumetric ratio of the second catalyst to the first catalyst is about 2:1 or greater, about 3:1 or greater, or about 4:1 or greater.

333. The process of any one of items 324 to 332, wherein the reaction zone comprises a second stage and the second stage comprises a mixture of the first catalyst and the second catalyst and the weight or volumetric ratio of the second catalyst to the first catalyst is from about 2:1 to about 10:1, from about 2:1 to about 5:1, from about 3:1 to about 10:1, or from about 3:1 to about 5:1.

334. The process of any one of items 324 to 333, wherein the ratio of the second catalyst to the first catalyst referred to is the volumetric ratio.

335. The process of any one of the preceding items, wherein the reaction zone comprises
  (i) a first stage and the first stage comprises a mixture of the first catalyst and the second catalyst and the volumetric ratio of the first catalyst to the second catalyst is from about 3:1 to about 5:1; and
  (ii) a second stage and the second stage comprises a mixture of the first catalyst and the second catalyst and the volumetric ratio of the second catalyst to the first catalyst is from about 3:1 to about 5:1.

336. The process of item 335, wherein
  in the first stage the weight ratio of the first catalyst to the second catalyst is from about 3:1 to about 1:1; and
  in the second stage the weight ratio of the second catalyst to the first catalyst is from about 4.5:1 to about 7.5:1.

337. The process of any one of items 324 to 336, wherein the volumetric ratio of the total amount of first catalyst to second catalyst in the reaction zone is from about 1:10 to about 10:1, from about 1:5 to about 5:1, from about 1:3 to about 3:1, or about 1:1.

338. The process of any one of items 324 to 337, wherein the first catalyst is a heterogeneous catalyst.

339. The process of any one of items 324 to 338, wherein the first catalyst comprises a catalyst support.

340. The process of item 339, wherein the support of the first catalyst comprises a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof.

341. The process of item 339 or 340, wherein the support of the first catalyst comprises carbon, titania, zirconia, or combinations thereof.

342. The process of any one of items 339 to 341, wherein the support of the first catalyst comprises at least one carbon material selected from the group consisting of graphite, carbon black, activated carbon and combinations thereof.

343. The process of any one of items 339 to 342, wherein the support of the first catalyst comprises carbon black.

344. The process of any one of items 339 to 343, wherein the first catalyst has a platinum loading of about 10 wt. % or less, about 7.5 wt. % or less, about 5 wt. % or less, about 4 wt. % or less, about 2 wt. % or less, or about 1 wt. % or less.

345. The process of any one of items 339 to 344, wherein the first catalyst has a platinum loading of about 0.1 wt. % or greater, about 0.25 wt. % or greater, about 0.5 wt. % or greater, about 0.75 wt. % or greater, or about 1 wt. % or greater.

346. The process of any one of items 339 to 345, wherein the first catalyst has a platinum loading of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 1 wt. % to about 10 wt. %, from about 1 wt. % to about 7.5 wt. %, from about 1 wt. % to about 5 wt. %, from about 1 wt. % to about 4 wt. %, or from about 1 wt. % to about 3 wt. %.

347. The process of any of items 339 to 346, wherein the first catalyst has a platinum loading of from about 0.1 wt. % to about 10 wt. %.

348. The process of any of items 339 to 347, wherein the first catalyst has a platinum loading of from about 0.1 wt. % to about 5 wt. %.

349. The process of any of items 339 to 348, wherein the first catalyst has a platinum loading of from about 0.5 wt. % to about 5 wt. %.

350. The process of any of items 339 to 349, wherein the first catalyst has a platinum loading of from about 1 wt. % to 5 wt. %.

351. The process of any one of items 339 to 350, wherein the first catalyst has a platinum loading of from about 1 wt. % to 4 wt. %.

352. The process of any one of items 339 to 351, wherein the second catalyst is a heterogeneous catalyst.

353. The process of any one of items 339 to 352, wherein the second catalyst comprises a catalyst support.

354. The process of item 353, wherein the support of the first catalyst is not the same as the support of the second catalyst.

355. The process of item 353 or 354, wherein the support of the second catalyst comprises a material selected from the group consisting of carbon, alumina, silica, ceria, titania, zirconia, niobia, zeolites, magnesia, clays, nickel, cobalt, copper, iron oxide, silicon carbide, aluminosilicates, montmorillonites, and combinations thereof.

356. The process of any one of items 353 to 355, wherein the support of the second catalyst comprises a material comprising carbon, alumina, silica, titania, zirconia, or combinations thereof.

357. The process of any one of items 353 to 356, wherein the support of the second catalyst comprises at least one carbon material selected from the group consisting of graphite, carbon black, activated carbon and combinations thereof.

358. The process of any one of items 353 to 357, wherein the support of the second catalyst comprises zirconia, doped zirconia, doped zirconia-metal composite, doped zirconia-metal oxide composite, titania, doped titania, doped titania-metal composite, doped titania-metal oxide composite, or mixtures thereof.

359. The process of any one of items 353 to 358, wherein the support of the second catalyst comprises titania.

360. The process of any one of items 324 to 359, wherein the second catalyst has a gold loading of about 10 wt. % or less, about 7.5 wt. % or less, about 5 wt. % or less, about 4 wt. % or less, about 2 wt. % or less, or about 1 wt. % or less.

361. The process of any one of items 324 to 360, wherein the second catalyst has a gold loading of about 0.1 wt. % or greater, about 0.25 wt. % or greater, about 0.5 wt. % or greater, about 0.75 wt. % or greater, or about 1 wt. % or greater.

362. The process of any one of items 324 to 361, wherein the second catalyst has a gold loading of from about 0.1 wt. % to about 10 wt. %, from about 0.1 wt. % to about 7.5 wt. %, from about 0.1 wt. % to about 5 wt. %, from about 0.1 wt. % to about 4 wt. %, from about 0.1 wt. % to about 3 wt. %, from about 0.1 wt. % to about 2 wt. %, from about 0.5 wt. % to about 10 wt. %, from about 0.5 wt. % to about 7.5 wt. %, from about 0.5 wt. % to about 5 wt. %, from about 0.5 wt. % to about 4 wt. %, from about 0.5 wt. % to about 3 wt. %, from about 0.5 wt. % to about 2 wt. %, from about 1 wt. % to about 10 wt. %, from about 1 wt. % to about 7.5 wt. %, from about 1 wt. % to about 5 wt. %, from about 1 wt. % to about 4 wt. %, from about 1 wt. % to about 3 wt. %, or from about 1 wt. % to about 2 wt. %.

363. The process of any one of items 324 to 362, wherein the second catalyst has a gold loading of from about 0.1 wt. % to about 10 wt. %.

364. The process of any one of items 324 to 363, wherein the second catalyst has a gold loading of from about 0.1 wt. % to about 5 wt. %.

365. The process of any one of items 324 to 364, wherein the second catalyst has a gold loading of from about 0.1 wt. % to about 2 wt. %.

366. The process of any one of items 324 to 365, wherein the second catalyst has a gold loading of from about 0.5 wt. % to about 2 wt. %.

367. The process of any one of items 324 to 366, wherein the second catalyst has a gold loading of from about 1.0 wt. % to about 2 wt. %.

368. The process of any one of items 324 to 367, wherein the first catalyst comprises a catalytically active phase and platinum constitutes about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the catalytically active phase.

369. The process of any one of items 324 to 368, wherein the first catalyst comprises a catalytically active phase and platinum constitutes from about 20 wt. % to about 99 wt. %, from about 30 wt. % to about 99 wt. %, from about 40 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 20 wt. % to about 95 wt. %, from about 30 wt. % to about 95 wt. %, from about 40 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 90 wt. % to about 95 wt. %, from about 20 wt. % to about 90 wt. %, from about 30 wt. % to about 90 wt. %, from about 40 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the catalytically active phase.

370. The process of any one of items 324 to 369, wherein the second catalyst comprises a catalytically active phase and gold constitutes about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the catalytically active phase.

371. The process of any one of items 324 to 370, wherein the second catalyst comprises a catalytically active phase and gold constitutes from about 20 wt. % to about 99 wt. %, from about 30 wt. % to about 99 wt. %, from about 40 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 20 wt. % to about 95 wt. %, from about 30 wt. % to about 95 wt. %, from about 40 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 90 wt. % to about 95 wt. %, from about 20 wt. % to about 90 wt. %, from about 30 wt. % to about 90 wt. %, from about 40 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the catalytically active phase.

372. The process of any one of the preceding items, wherein the process is conducted in the absence of added base.

373. The process of any one of the preceding items, wherein the pH of the reaction mixture is not controlled or increased by the addition of base.

374. The process of any one of the preceding items, wherein base is not fed to the reaction zone.

375. The process of any one of the preceding items, wherein the reaction mixture and/or reaction zone is free or essentially free of salt-forming cations.

376. The process of any one of the preceding items, wherein the pH of the reaction mixture measured at 20° C. is about 7 or less, about 6.5 or less, about 6 or less, about 5 or less, about 4 or less, about 3 or less, or about 2 or less.

377. The process of any one of the preceding items, wherein the pH of the reaction mixture(s) measured at 20° C. is about 7 or less, about 6.5 or less, about 6 or less, about 5 or less, about 4 or less, about 3 or less, or about 2 or less.

378. The process of any one of the preceding items, wherein the pH of the reaction mixture(s) measured at 20° C. is from about 1 to about 7, from about 1 to about 6, from about 1 to about 5, from about 1 to about 4, from about 1.5 to about 7, from about 1.5 to about 6, from about 1.5 to about 5, from about 1.5 to about 4, from about 2 to about 7, from about 2 to about 6, from about 2 to about 5, or from about 2 to about 4.

379. The process of any one of the preceding items, wherein the pH of the reaction mixture(s) measured at 20° C. is from about 1 to about 2.

380. The process of any one of the preceding items, wherein the reaction zone comprises one or more trickle bed reactors.

381. The process of any one of the preceding items, wherein the reaction zone comprises one or more fixed bed reactors.

382. The process of any one of the preceding items, wherein the liquid hourly space velocity (LHSV) of the reaction zone is about $0.2\ hr^{-1}$ or greater, about $0.5\ hr^{-1}$ or greater, about $1\ hr^{-1}$ or greater, about $1.5\ hr^{-1}$ or greater, about $2\ hr^{-1}$ or greater, about $5\ hr^{-1}$ or greater, or about $10\ hr^{-1}$ or greater.

383. The process of any one of the preceding items, wherein the LHSV of the reaction zone is from about $0.2\ h^{-1}$ to about $50\ hr^{-1}$, about $0.5\ h^{-1}$ to about $50\ hr^{-1}$, or about $1\ hr^{-1}$ to about $50\ h^{-1}$, from about $2\ h^{-1}$ to about $50\ hr^{-1}$, about $5\ hr^{-1}$ to about $50\ h^{-1}$, or about $10\ hr^{-1}$ to about $50\ hr^{-1}$, from about $0.2\ h^{-1}$ to about $10\ hr^{-1}$, about $0.5\ h^{-1}$ to about $10\ h^{-1}$, about $1\ hr^{-1}$ to about $10\ h^{-1}$, from about $2\ h^{-1}$ to about $10\ hr^{-1}$, or about $5\ hr^{-1}$ to about $10\ hr^{-1}$.

384. The process of any one of the preceding items, wherein the LHSV of the reaction zone is from about $0.2\ h^{-1}$ to about $5\ h^{-1}$.

385. The process of any one of the preceding items, wherein the LHSV of the reaction zone is from about $0.2\ h^{-1}$ to about $4\ h^{-1}$.

386. The process of any one of the preceding items, wherein the LHSV of the reaction zone is from about $0.4\ h^{-1}$ to about $2.5\ h^{-1}$.

387. The process of any one of the preceding items, wherein the LHSV of the reaction zone is from about $0.5\ h^{-1}$ to about $2\ h^{-1}$.

388. The process of any one of the preceding items, wherein the reaction zone is heated to a temperature of about 60° C. or greater, about 70° C. or greater, or about 80° C. or greater.

389. The process of any one of the preceding items, wherein the reaction zone is heated to a temperature of from about 60° C. to about 150° C., from about 70° C. to about 150° C., from about 80° C. to about 150° C., from about 60° C. to about 125° C., from about 70° C. to about 125° C., from about 80° C. to about 125° C., from about 60° C. to about 100° C., from about 70° C. to about 100° C., or from about 80° C. to about 100° C.

390. The process of any one of the preceding items, wherein the reaction zone is heated to a temperature of from about 70° C. to about 110° C.

391. The process of any one of the preceding items, wherein the reaction zone is heated to a temperature of from about 75° C. to about 110° C.

392. The process of any one of the preceding items, wherein the reaction zone is heated to a temperature of from about 80° C. to about 110° C.

393. The process of any one of the preceding items, wherein the reaction zone is heated to a temperature of from about 80° C. to about 100° C.

394. The process of any one of the preceding items, wherein the partial pressure of oxygen in the reaction zone is about 2 psig or greater, about 25 psig or greater, about 50 psig or greater, or about 100 psig or greater, or in the range of from about 2 psig to about 2000 psig, from about 50 psig to about 2000 psig, or from about 100 psig to about 2000 psig.

395. The process of any one of the preceding items, wherein the partial pressure of oxygen is from about 2 psig to about 2000 psig.

396. The process of any one of the preceding items, wherein the partial pressure of oxygen is from about 50 psig to about 2000 psig.

397. The process of any one of the preceding items, wherein the partial pressure of oxygen is from about 75 psig to about 250 psig.

398. The process of any one of the preceding items, wherein the oxygen is supplied to the reaction zone as an oxygen-containing gaseous mixture.

399. The process of any one of the preceding items, wherein the oxygen is supplied to the reaction zone as air, oxygen-enriched air, a mixture comprising at least about 40 or 50 vol. % oxygen, a mixture comprising oxygen and nitrogen (e.g., about 50:50 mixture by volume), or substantially pure oxygen (at least 99 vol. % oxygen).

400. The process of any one of the preceding items, wherein the oxygen is supplied to the reaction zone as a mixture having an oxygen concentration of about 0.5 vol. % or greater, about 1 vol. % or greater, about 5 vol. % or greater, or about 10 vol. % or greater.

401. The process of any one of the preceding items, wherein the oxygen is supplied to the reaction zone as a mixture having an oxygen concentration from about 0.5 vol. % to about 20 vol. %, from about 0.5 vol. % to about 15 vol. %, from about 0.5 vol. % to about 10 vol. %, from about 0.5 vol. % to about 5 vol. %, from about 1 vol. % to about 20 vol. %, from about 1 vol. % to about 15 vol. %, from about 1 vol. % to about 10 vol. %, from about 1 vol. % to about 5 vol. %, from about 5 vol. % to about 20 vol. %, from about 5 vol. % to about 15 vol. %, or from about 5 vol. % to about 10 vol. %.

402. The process of any one of the preceding items, wherein the oxygen is supplied to the reaction zone as a mixture having an oxygen concentration from about 5 vol. % to about 20 vol. %.

403. The process of any one of the preceding items, wherein the process is not an electrochemical process.

404. The process of any one of the preceding items, wherein the process does not comprise applying an electric current to the reaction mixture.

405. A process for analyzing a feed mixture comprising at least one feed component selected from the group consisting of a $C_5$-$C_6$ aldose, a $C_5$-$C_6$ aldonic acid and/or lactone(s) thereof, a $C_5$-$C_6$ uronic acid and/or lactone(s) thereof, a $C_5$-$C_6$ aldaric acid and/or lactone(s) thereof, and mixtures thereof, the process comprising:

analyzing the feed mixture to determine the components of the feed mixture and to determine the presence or any oxidation reaction inhibitor(s), wherein the oxidation reaction inhibitor is a compound that inhibits the oxidation of the at least one feed component selected from the group consisting of a $C_5$-$C_6$ aldose, a $C_5$-$C_6$ aldonic acid and/or lactone(s) thereof, a $C_5$-$C_6$ uronic acid and/or lactone(s) thereof, a $C_5$-$C_6$ aldaric acid and/or lactone(s) thereof, and mixtures thereof.

406. The process of item 405, further comprising determining an oxidation inhibition factor for one or more components of the feed mixture, wherein the oxidation inhibition factor is the percentage by which a reaction performance factor is reduced at a given concentration of the oxidation reaction inhibitor.

407. The process of item 406, wherein the reaction performance factor is selected from the group consisting of yield of an oxidation product, selectivity to an oxidation product, catalyst efficiency, yield of one or more off-path products, and combinations thereof.

408. The process of item 406 or 407, wherein the oxidation inhibition factor is determined by comparing the results of a first oxidation reaction and a second oxidation reaction where the reaction mixtures and conditions for the first oxidation reaction and second oxidation reaction are the same except that the reaction mixture of the second oxidation reaction contains a greater concentration of a component of the feed mixture that is being evaluated as an oxidation reaction inhibitor.

409. The process of item 408, wherein a component of the feed mixture is an oxidation reaction inhibitor if the oxidation inhibition factor is about 5% or greater, about 10% or greater, about 20% or greater, about 30% or greater, about 40% or greater, or about 50% or greater.

410. The process of item 409, wherein a component of the feed mixture is an oxidation reaction inhibitor if the oxidation inhibition factor is about 5% or greater.

411. The process of item 409, wherein a component of the feed mixture is an oxidation reaction inhibitor if the oxidation inhibition factor is about 10% or greater.

412. The process of item 409, wherein a component of the feed mixture is an oxidation reaction inhibitor if the oxidation inhibition factor is about 20% or greater.

413. The process of item 409, wherein a component of the feed mixture is an oxidation reaction inhibitor if the oxidation inhibition factor is about 30% or greater.

414. The process of item 409, wherein a component of the feed mixture is an oxidation reaction inhibitor if the oxidation inhibition factor is about 40% or greater.

415. The process of item 409, wherein a component of the feed mixture is an oxidation reaction inhibitor if the oxidation inhibition factor is about 50% or greater.

416. A process for producing an upgraded feed mixture, the process comprising:
analyzing the feed mixture according to any one of items 405 to 415 to determine the presence of an oxidation reaction inhibitor; and
separating at least a portion of the oxidation reaction inhibitor from the feed mixture in a separation zone to form a first fraction comprising the upgraded feed mixture and a second fraction comprising at least a portion of the oxidation reaction inhibitor.

417. The process of item 416, further comprising, separating at least a portion of the oxidation reaction inhibitor when the oxidation reaction inhibitor has an oxidation inhibitor factor exceeding a threshold value.

418. The process of item 417, wherein the threshold value is about 5% or greater, about 10% or greater, about 20% or greater, about 30% or greater, about 40% or greater, or about 50% or greater.

419. The process of item 418, wherein the threshold value is about 5% or greater.

420. The process of item 418, wherein the threshold value is about 10% or greater.

421. The process of item 418, wherein the threshold value is about 20% or greater.

422. The process of item 418, wherein the threshold value is about 30% or greater.

423. The process of item 418, wherein the threshold value is about 40% or greater.

424. The process of item 418, wherein the threshold value is about 50% or greater.

425. The process of any one of items 416 to 424, wherein the separation zone comprises a chromatographic separation stage.

426. The process of item 425, wherein the chromatographic separation stage comprises a separation media.

427. The process of item 426, wherein the separation media comprises an amphoteric and/or anionic chromatography resin.

428. The process of any one of items 416 to 427, wherein the concentration of the oxidation reaction inhibitor in the upgraded feed mixture is about 0.5 wt. % or less, about 0.3 wt. % or less, about 0.1 wt. % or less, about 0.05 wt. % or less, or about 0.01 wt. % or less.

429. The process of item 428, wherein the concentration of the oxidation reaction inhibitor in the upgraded feed mixture is about 0.5 wt. % or less.

430. The process of item 428, wherein the concentration of the oxidation reaction inhibitor in the upgraded feed mixture is about 0.3 wt. % or less.

431. The process of item 428, wherein the concentration of the oxidation reaction inhibitor in the upgraded feed mixture is about 0.1 wt. % or less.

432. The process of item 428, wherein the concentration of the oxidation reaction inhibitor in the upgraded feed mixture is about 0.05 wt. % or less.

433. The process of item 428, wherein the concentration of the oxidation reaction inhibitor in the upgraded feed mixture is about 0.01 wt. % or less.

434. The process of any one of items 416 to 433, wherein the concentration of the oxidation reaction inhibitor in the upgraded feed mixture is from about 0.001 wt. % to about 0.5 wt. %, from about 0.001 wt. % to about 0.1 wt. %, from about 0.001 wt. % to about 0.05 wt. %, from about 0.001 wt. % to about 0.01 wt. %, from about 0.005 wt. % to about 0.5 wt. %, from about 0.005 wt. % to about 0.1 wt. %, from about 0.005 wt. % to about 0.05 wt. %, from about 0.005 wt. % to about 0.01 wt. %, from about 0.01 wt. % to about 0.5 wt. %, from about 0.01 wt. % to about 0.1 wt. %, from about 0.01 wt. % to about 0.05 wt. %, from about 0.05 wt. % to about 0.5 wt. %, from about 0.05 wt. % to about 0.1 wt. %, or from about 0.1 wt. % to about 0.5 wt. %.

435. The process of item 434, wherein the concentration of the oxidation reaction inhibitor in the upgraded feed mixture is from about 0.001 wt. % to about 0.5 wt. %.

436. The process of item 434, wherein the concentration of the oxidation reaction inhibitor in the upgraded feed mixture is from about 0.001 wt. % to about 0.1 wt. %.

437. The process of item 434, wherein the concentration of the oxidation reaction inhibitor in the upgraded feed mixture is from about 0.001 wt. % to about 0.05 wt. %.

438. The process of item 434, wherein the concentration of the oxidation reaction inhibitor in the upgraded feed mixture is from about 0.001 wt. % to about 0.01 wt. %.

439. The process of item 434, wherein the concentration of the oxidation reaction inhibitor in the upgraded feed mixture is from about 0.005 wt. % to about 0.5 wt. %.

440. The process of item 434, wherein the concentration of the oxidation reaction inhibitor in the upgraded feed mixture is from about 0.005 wt. % to about 0.1 wt. %.

441. The process of item 434, wherein the concentration of the oxidation reaction inhibitor in the upgraded feed mixture is from about 0.005 wt. % to about 0.05 wt. %.

442. The process of item 434, wherein the concentration of the oxidation reaction inhibitor in the upgraded feed mixture is from about 0.005 wt. % to about 0.01 wt. %.
443. The process of item 434, wherein the concentration of the oxidation reaction inhibitor in the upgraded feed mixture is from about 0.01 wt. % to about 0.5 wt. %.
444. The process of item 434, wherein the concentration of the oxidation reaction inhibitor in the upgraded feed mixture is from about 0.01 wt. % to about 0.1 wt. %.
445. The process of item 434, wherein the concentration of the oxidation reaction inhibitor in the upgraded feed mixture is from about 0.01 wt. % to about 0.05 wt. %.
446. The process of item 434, wherein the concentration of the oxidation reaction inhibitor in the upgraded feed mixture is from about 0.05 wt. % to about 0.5 wt. %.
447. The process of item 434, wherein the concentration of the oxidation reaction inhibitor in the upgraded feed mixture is from about 0.05 wt. % to about 0.1 wt. %.
448. The process of item 434, wherein the concentration of the oxidation reaction inhibitor in the upgraded feed mixture is from about 0.1 wt. % to about 0.5 wt. %.
449. The process of any one of items 416 to 448, wherein the concentration of the oxidation reaction inhibitor in the upgraded feed mixture is reduced by about 50 wt. % or more, by about 60 wt. % or more, by about 70 wt. % or more, by about 80 wt. % or more, or by about 90 wt. % or more as compared to the concentration in the feed mixture prior to separation.
450. The process of item 449, wherein the concentration of the oxidation reaction inhibitor in the upgraded feed mixture is reduced by about 50 wt. % or more as compared to the concentration in the feed mixture prior to separation.
451. The process of item 449, wherein the concentration of the oxidation reaction inhibitor in the upgraded feed mixture is reduced by about 60 wt. % or more as compared to the concentration in the feed mixture prior to separation.
452. The process of item 449, wherein the concentration of the oxidation reaction inhibitor in the upgraded feed mixture is reduced by about 70 wt. % or more as compared to the concentration in the feed mixture prior to separation.
453. The process of item 449, wherein the concentration of the oxidation reaction inhibitor in the upgraded feed mixture is reduced by about 80 wt. % or more as compared to the concentration in the feed mixture prior to separation.
454. The process of item 449, wherein the concentration of the oxidation reaction inhibitor in the upgraded feed mixture is reduced by about 90 wt. % or more as compared to the concentration in the feed mixture prior to separation.
455. The process of any one of items 405 to 454, wherein the oxidation reaction inhibitor comprises a $C_3$ alcohol and/or a $C_3$ acid.
456. The process of item 455, wherein the oxidation reaction inhibitor comprises a $C_3$ alcohol.
457. The process of item 455, wherein the oxidation reaction inhibitor comprises a $C_3$ acid.
458. The process of item 455, wherein the oxidation reaction inhibitor comprises a $C_3$ alcohol and a $C_3$ acid.
459. The process of any one of items 405 to 458, wherein the oxidation reaction inhibitor comprises at least one component selected from the group consisting of glyceric acid, 3-hydroxypropionic acid, 1,3-propanediol, and mixtures thereof.
460. The process of any one of items 405 to 459, wherein the oxidation reaction inhibitor comprises glyceric acid.
461. The process of any one of items 405 to 460, wherein the oxidation reaction inhibitor comprises 3-hydroxypropionic acid.

The invention claimed is:

1. A process for preparing a $C_5$-$C_6$ aldaric acid and/or lactone(s) thereof via catalytic oxidation from a feed mixture comprising an oxidation reaction inhibitor, the process comprising:
    feeding a feed mixture comprising
    (a) at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof, and
    (b) an oxidation reaction inhibitor
    to a separation zone to separate at least a portion of the oxidation reaction inhibitor from the feed mixture and form a first fraction comprising at least a portion of the oxidation reactant and a second fraction comprising at least a portion of the oxidation reaction inhibitor;
    feeding at least a portion of the first fraction comprising the oxidation reactant to a reaction zone; and
    reacting the oxidation reactant in the presence of oxygen and an oxidation catalyst in the reaction zone to form a reaction mixture comprising the $C_5$-$C_6$ aldaric acid and/or lactone(s) thereof; wherein
        (i) the oxidation reaction inhibitor comprises a $C_3$ alcohol and/or a $C_3$ acid, and
        (ii) the concentration of said oxidation reaction inhibitor in the first fraction is about 0.5 wt. % or less.

2. The process of claim 1, wherein the molar ratio of the oxidation reaction inhibitor to the oxidation reactant in the first fraction is less than the molar ratio of the oxidation reaction inhibitor to oxidation reactant in the feed mixture.

3. The process of claim 1 or 2, wherein the molar ratio of the oxidation reaction inhibitor to oxidation reactant in the first fraction is less than the molar ratio of the oxidation reaction inhibitor to oxidation reactant in the second fraction.

4. The process of claim 1, wherein the concentration of the oxidation reactant in the first fraction is from about 1 wt. % to 50 wt. %.

5. A process for preparing a $C_5$-$C_6$ aldaric acid and/or lactone(s) thereof via catalytic oxidation from a feed mixture comprising an oxidation reaction inhibitor, the process comprising:
    feeding a feed mixture comprising at least one oxidation reactant selected from the group consisting of a $C_5$-$C_6$ aldose, a $C_5$-$C_6$ aldonic acid and/or lactone(s) thereof, a $C_5$-$C_6$ uronic acid and/or lactone(s) thereof, and mixtures thereof to a reaction zone;
    reacting the oxidation reactant in the presence of oxygen and an oxidation catalyst in the reaction zone to form a reaction mixture comprising (a) the $C_5$-$C_6$ aldaric acid and/or lactone(s) thereof, (b) unreacted oxidation reactant(s) and/or on-path intermediate(s) thereof, and (c) an oxidation reaction inhibitor;
    feeding the reaction mixture to a separation zone to separate at least a portion of the $C_5$-$C_6$ aldaric acid and/or lactone(s) thereof from the reaction mixture and form a product fraction comprising the $C_5$-$C_6$ aldaric acid and/or lactone(s) thereof and a recycle fraction comprising the unreacted oxidation reactant(s) and/or on-path intermediate(s) thereof and the oxidation reaction inhibitor;
    removing a first portion of the recycle fraction from the process; and
    recycling a second portion of the recycle fraction to the reaction zone or feed thereto; wherein
        (i) the oxidation reaction inhibitor comprises a $C_3$ alcohol and/or a $C_3$ acid, and (ii) the concentration of said oxidation reaction inhibitor in the second portion of the recycle fraction is about 0.5 wt. % or less.

6. The process of claim 5, wherein the concentration of the oxidation reaction inhibitor in the second portion of the recycle fraction is about 0.3 wt. % or less, about 0.1 wt. % or less, about 0.05 wt. % or less, or about 0.01 wt. % or less.

7. The process of claim 5, wherein the separation zone comprises a chromatographic separation stage.

8. The process of claim 7, wherein the chromatographic separation stage comprises a separation media.

9. The process of claim 8, wherein the separation media comprises an amphoteric and/or anionic chromatography resin.

10. The process of claim 1 or claim 5, wherein the oxidation reactant comprises the $C_5$-$C_6$ aldose, in particular wherein said $C_5$-$C_6$ aldose is selected from the group consisting of arabinose, lyxose, ribose, xylose, allose, altrose, galactose, glucose, gulose, idose, mannose, talose, and mixtures thereof.

11. The process of claim 1 or claim 5, wherein the oxidation reactant comprises the $C_5$-$C_6$ aldonic acid and/or lactone(s) thereof, in particular wherein the $C_5$-$C_6$ aldonic acid is selected from the group consisting of arabinonic acid, lyxonic acid, ribonic acid, xylonic acid, allonic acid, altronic acid, galactonic acid, gluconic acid, gulonic acid, idonic acid, mannonic acid, talonic acid, and mixtures thereof.

12. The process of claim 1 or claim 5, wherein the oxidation reactant comprises the $C_5$-$C_6$ uronic acid and/or lactone(s) thereof, in particular wherein the $C_5$-$C_6$ uronic acid is selected from the group consisting of arabinuronic acid, lyxonuronic acid, ribouronic acid, xylouronic acid, alluronic acid, altruronic acid, galactouronic acid, glucuronic acid, guluronic acid, iduronic acid, mannouronic acid, talonuronic acid, and mixtures thereof.

13. The process of claim 1 or claim 5, wherein the oxidation catalyst comprises a catalytically active phase, and wherein said catalytically active phase comprises one or more noble metals.

14. The process of claim 13, wherein the catalytically active phase comprises platinum and/or gold.

* * * * *